(12) United States Patent
Janaky et al.

(10) Patent No.: US 6,214,969 B1
(45) Date of Patent: *Apr. 10, 2001

(54) LUTEINIZING HORMONE RELEASING HORMONE ANALOGS WITH CYTOTOXIC MOIETY

(75) Inventors: Tamas Janaky, Szeged; Attila Juhasz; Sandor Bajusz, both of Budapest, all of (HU); Andrew V. Schally, Metairie, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/008,186

(22) Filed: Jan. 25, 1993

Related U.S. Application Data

(63) Continuation-in-part of application No. 07/505,517, filed on Apr. 6, 1990, now abandoned, which is a continuation-in-part of application No. 07/404,667, filed on Sep. 7, 1989, now abandoned, which is a continuation-in-part of application No. 07/260,994, filed on Oct. 21, 1988, now abandoned.

(51) Int. Cl.$^7$ .................................................... C07K 7/23
(52) U.S. Cl. .......................... 530/313; 530/328; 530/816; 530/810; 514/15; 514/800; 424/195.11; 424/193.1; 424/198.1; 930/110
(58) Field of Search .................................... 530/313, 328, 530/816, 810; 930/110; 514/15, 800; 424/195.11, 198.1, 193.1

(56) References Cited

U.S. PATENT DOCUMENTS

| | | | |
|---|---|---|---|
| 4,652,550 | * 3/1987 | Rivier et al. | 530/313 |
| 4,713,366 | * 12/1987 | Stevens | 930/110 |
| 5,169,933 | * 12/1992 | Anderson et al. | 530/313 |

FOREIGN PATENT DOCUMENTS

2185486 * 7/1987 (GB).

WO90/09799 9/1990 (WO).

OTHER PUBLICATIONS

Szepeshazi et al., Anti–Cancer Drugs, 3 109–116 (1992).
Communication Pursuant to Article 96(2) and Rue 51(2) EPC—Oct. 27, 1992.
European Search Report, Jan. 24, 1992, EP 91 10 4730.
Proc. Nat'l. Acad. Sci., Bajusz et al, vol. 86, pp. 6318–6322, (Aug. 1989).*
Peptides, Proceedings of the Sixth American Pept. Symposium, E. Gross and J. Heienhofer (eds.), pp. 803–806.*

* cited by examiner

*Primary Examiner*—T. D. Wessendorf
(74) *Attorney, Agent, or Firm*—Selitto & Associates, P.C.

(57) ABSTRACT

The present invention deals with LHRH analogs which contain cytotoxic moieties, have influence on the release of gonadotropins from the pituitary in mammals (possess high agonistic or antagonistic activity) and have antineoplastic effect. The compounds of this invention are represented by Formula I: $X-R^1-R^2-R^3-Ser-R^5-R^6(Q)-Leu-Arg-Pro-R^{10}-NH_2$, wherein $R^1$ is pGlu or D-Nal(2), $R^2$ is His or D-Phe (4Cl), $R^3$ is Trp, D-Trp or D-Pal(3), $R^5$ is Tyr or Arg, $R^6$ is D-Lys or D-Orn, $R^{10}$ is Gly or D-Ala, X is hydrogen or a lower alkanoyl group of 2–5 carbon atoms, Q is a cytotoxic moiety having the formula $—Q^4$ or $—A(Q^3)$ or $—B(Q^1)_2$ or $—B(AQ^2)_2$, wherein A is $—NH—(CH_2)_n—CO—$ or $—OC—(CH_2)_n—CO—$ where n is 2–6, B is $—NH—CH_2—(CH_2)_m—CH(NH)—(CH_2)_n—CO—$ where m is 0 or 1, n is 0 or 1, the —CO moiety of A— and of B— being bonded to an amino group on $R^6$, and in the group $B(AQ^2)_2$, the —CO moiety of A— and of B— being bonded to the episilon or delta amino group of $R^6$ when $R^6$ is Lys or Orn respectively, and in the group $B(AQ^2)_2$, the —CO moiety of A being bonded to an amino group on B, $Q^1$ is D or L-Mel, cyclopropanealkanoyl, aziridine-2-carbonyl, epoxyalkyl or 1,4-naphthoquinone-5-oxy-carbonyl-ethyl, $Q^2$ is $Q^1$, 2-anthraquinonyl-methylenoxy or doxorubicinyl, $Q^3$ is $Q^2$, mitomicinyl, esperamycinyl or methotrexoyl, $Q^4$ is $Q^1$ or methotrexoyl and pharmaceutically acceptable salts thereof and methods of use pertaining these compounds.

23 Claims, No Drawings

LUTEINIZING HORMONE RELEASING HORMONE ANALOGS WITH CYTOTOXIC MOIETY

RELATED APPLICATIONS

This application is a continuation-in-part of copending application, Ser. No. 07/505,517, filed Apr. 6, 1990, abandoned, which was a continuation in part of Ser. No. 07/404,667, filed Sep. 07, 1989, abandoned, itself a continuation-in-part of Ser. No. 07/260,994, filed Oct. 21, 1988, abandoned.

This invention was made with Government support under grant Nos. 40003 and 40004, awarded by the N.C.I. (NIH). The U.S. Government has certain rights in this application.

BACKGROUND OF THE INVENTION

The present invention relates to novel peptides which contain cytotoxic moieties, have influence on the release of gonadotropins from the pituitary in mammals and possess antineoplastic effect. More specifically, the present invention relates to analogs of luteinizing hormone-releasing hormone (LHRH) with the structure of

pGlu-His-Trp-Ser-Tyr-Gly-Leu-Arg-Pro-Gly-NH$_2$ salts thereof and to pharmaceutical compositions and methods of using these analogs.

DISCUSSION OF THE PRIOR ART

Hypothalamic luteinizing hormone-releasing hormone (LHRH) controls the pituitary release of gonadotropins (LH and FSH) that stimulate the synthesis of sex steroids in the gonads.

A new approach in the treatment of hormone-sensitive tumors has been developed directed to the use of agonists and antagonists of LHRH (A. V. Schally and A. M. Comaru-Schally, Sem. Endocrinol., 5 389–398, 1987). Some LHRH agonists, when substituted in position 6, 10, or both are much more active than LHRH and also possess prolonged activity. The following superagonists are used in the clinical practice:

[D-Leu[6], NH-Et[10]]LHRH (Leuprolide; J. A. Vilchez-Martinez et al., Biochem. Biophys. Res. Commun., 59 1226–1232, 1974)

[D-Trp[6]]LHRH (Decapeptyl, D. H. Coy et al., J.Med.Chem., 19 423–425, 1976).

[D-Ser(tBu)[6],NH-Et[10]]LHRH (Buserelin, W. Koenig et al., In: R. Walter and J. Meienhofer (eds.), Peptides: Chemistry, Structure and Biology. Proceedings of the Fourth American Peptide Symposium. Ann Arbor Science, Ann Arbor, Mich., 1975, pp. 883–888.

[D-Ser(tBu)[6],NH—NH—CO—NH$_2$[10]]LHRH (Zoladex, A. S. Dutta et al., J. Med. Chem., 21 1018–1024, 1978).

[D-Nal(2)[6]]LHRH (Nafarelin, J. J. Nestor et al., J. Med. Chem., 25 795–801, 1982).

Changes in position 1, 2, 3, 6 and optionally in positions 5 and 10 of the LHRH molecule led to the creation of powerful antagonists (M. J. Karten and J. E. Rivier, Endocrine Review, 7 44–66, 1986; S. Bajusz et al., Int. J. Pept. Prot. Res., 32 425–435, 1988) which inhibit the LH and FSH release from the pituitary and have potential as therapeutic agents in the treatment of hormone dependent cancers (prostate, breast and pancreatic) (A. V. Schally, in General Gynecology, Vol 6., Parthenon Press, Carnforth, England, 1989, pp. 1–20).

Ideal anticancer drugs would theoretically be those that eradicate cancer cells without harming normal cells. Hormones carrying antineoplastic agents would solve the problem by achieving more efficiently targeted chemotherapy of receptor-containing tumors. An ideal mechanism of action of hormone-drug conjugates would be their binding to a cell membrane receptor, followed by internalization of the hybrid molecules and release of the drugs or their biologically active derivatives from the carrier hormone in the endosomes or secondary lysosomes. The released substances then pass across the membrane of the vesicles into the cytosol and reach their final target sites. For the conjugates to be effective by this mechanism, the bond between the drug and hormone must be stable before internalization of conjugates into the target tumor cells but should be effectively cleaved after this internalization.

Many human tumors are hormone dependent or hormone-responsive and contain hormone receptors. Certain of these tumors are dependent on or responsive to sex hormones or growth factors or have components which are so dependent or responsive. The remaining tumors or tumor components are not so dependent. Mammary carcinomas contain estrogen, progesterone, glucocorticoid, LHRH, EGF, IGF-I. and somatostatin receptors. Peptide hormone receptors have also been detected in acute leukaemia, prostate-, breast-, pancreatic, ovarian-, endometrial cancer, colon cancer and brain tumors (M. N. Pollak, et al., Cancer Lett. 38 223–230, 1987; F. Pekonen, et al., Cancer Res., 48 1343–1347, 1988; M. Fekete, et al., J. Clin.Lab. Anal. 3 137–147, 1989; G. Emons, et al., Eur. J. Cancer Oncol., 25 215–221, 1989). It has been found (M. Fekete, et al., Endocrinology, 124 946–955, 1989; M. Fekete, et al.Pancreas 4 521–528, 1989) that both agonistic and antagonistic analogs of LHRH bind to human breast cancer cell membranes, and also to the cell membranes of pancreatic cancer, although the latter tumor thought to be hormone-independent. It has been demonstrated that biologically active peptides such as melanotropin (MSH), epidermal growth factor, insulin and agonistic and antagonistic analogs of LHRH (L. Jennes, et. al., Peptides 5 215–220, 1984) are internalized by their target cells by endocytosis.

Alkylating agents used in the treatment of cancer have a basically nonselective mechanism of action. They act by exerting the cytotoxic effect via transfer of their alkyl groups to various cell constituents. Alkylation of DNA within the nucleus probably represents the major interaction that leads to cell death. However, under physiologic conditions, one can alkylate all cellular nucleophiles such as ionized carboxylic and phosphoric acid groups, hydroxyl groups, thiols and uncharged nitrogen moieties. Nitrogen mustards (chlorambucil, cyclophosphamide and melphalan) are among the oldest anticancer drugs in clinical use. They spontaneously form cyclic aziridinium (ethylenimonium) cation derivatives by intramolecular cyclization, which may directly or through formation of a carbonium ion, transfer an alkyl group to a cellular nucleophile. Aziridine moiety containing drugs like thio-TEPA act by the same mechanism.

Cyclopropane is another alkylating agent. The highly strained ring is prone to cleavage by nucleophiles. It can be cleaved to singlet biradical transition and zwitterion transition state in epimerization reactions and thus might act as an alkylating species for interaction with nucleophilic bases of DNA. Incorporation of cyclopropyl group into distamycin (natural antiviral antitumor agent) resulted in four fold increase in cytostatic activity (K. Krowicki, et al., J. Med. Chem. 31 341–345, 1988).

Almost all clinically used alkylating agents are bifunctional and have ability to cross-link two separate molecules, or alkylate one molecule at two separate nucleophilic sites. The cross-links with DNA may be within a single strand, between two complementary strands or between DNA and other molecules, such as proteins. It is thought that the cytotoxicity of alkylating agents is correlated with their cross-linking efficiency (J. J. Roberts et al., Adv. Radiat. Biol. 7 211–435, 1978).

Cisplatin (cis-diaminedichloroplatinum) has been used in the cancer therapy for a long time. LHRH analogs with cisplatin related structure in the side-chain have high affinities for membrane receptors of rat pituitary and human breast cancer cells (S. Bajusz et al. Proc. Natl. Acad. Sci. USA 86 6313–6317, 1989). Incorporation of cytotoxic copper(II) and nickel(II) complexes into suitably modified LHRH analogs resulted in compounds with high hormonal activity and affinity for LHRH receptors on human breast cancer cell membrane. Several of these metallopeptides have cytotoxic activity against human breast and prostate cell lines in vitro. For example pGlu-His-Trp-Ser-Tyr-D-Lys[Ahx-A$_2$bu(SAL)$_2$(Cu)]-Leu-Arg-Pro-Gly-NH$_2$ inhibits the [$^3$H]thymidine incorporation into DNA of the human mammary cell line MDA-MB-231 by 87% at 10 µg dose.

Many drugs used in cancer chemotherapy contain the quinone group in their structure. Anthracycline antitumor antibiotics such as adriamycin, daunorubicin, mitomycin C and mitoxantrone bind to DNA through intercalation between specific bases and block the synthesis of new RNA or DNA (or both), cause DNA strand scission, and interfere with cell replication. Bioreductive reactions of the quinone group can lead to formation of free radicals (superoxide and hydroxyl radicals) that can induce DNA strand breaks (Bachur et al. Cancer Res. 38 1745–1750, 1978). An alternative pathway is the reduction of quinone to hydroquinone followed by conversion into the alkylating intermediate, the quinonemethide (Moore et al., Drug Exp. Clin. Res. 12 475–494, 1986). Daunorubicin was coupled to peptide carrier melanotropin (MSH) and the conjugate proved to be more toxic to murine melanoma cells than free drug (J. M. Varga, Meth. Enzymol. 112 259–269, 1985). 2-Methylanthraquinone derivatives have cytotoxic activity on hypoxic neoplastic cells (T. S. Lin, et al. J. Med. Chem. 23 1237–1242, 1980).

Several antimetabolites are of potential chemotherapeutic interest because of their importance in cellular folate metabolism (I. D. Goldman, et al., Eds. Folyl and Antifolyl Polyglutamates. Plenum press, New York, 1983.). Methotrexate {N-[p[[(2,4-diamino-6-pteridinyl)methyl]methylamino]benzoyl]glutamic acid is a folic acid antagonist that inhibits the function of dihydrofolate reductase and in this way interrupts the synthesis of thymidilate, purine nucleotides, and the amino acids serine and methionine, thereby interfering with the formation of DNA, RNA, and proteins.

Initially the incorporation of the alkylating drug chlorambucil {4-[4-(bis[2-chloroethyl]amino)phenyl}-butyric acid into LHRH agonist and antagonists led to compounds with low activity or no activity [K. Channabasavaiah and J. M. Stewart, Biochem. Biophys. Res. Commun., 86, 1266–1273 (1979), C. Y. Bowers et al., Biochem. Biophys. Res. Commun., 61, 698–703 (1974), K. Channabasavaiah et al., In: E. Gross and J. Meienhofer (eds.), Peptides, Proceedings of the Sixth American Peptide Symposium, Pierce Chem. Co. Rockford, Ill., 1979, pp 803–807].

D-melphalan (a nitrogen mustard type alkylating agent, 4-[bis{2-chloroethyl}amino]-D-phenylalanine) containing LHRH analogs have high agonistic and antagonistic activity and bind to the rat pituitary, human breast and prostate cancer cell membranes with high affinity (S. Bajusz et al., Proc. Natl. Acad. Sci. USA 86 6318–6322, 1989). The binding is reversible and no alkylation of the LHRH receptors occurred. Significant cytotoxic activity (inhibition of [$^3$H]thymidine incorporation) in cultures of human breast cancer cell line T-47D and rat mammary tumor cell line MT-4 and MT-5 could be demonstrated.

SUMMARY OF THE INVENTION

Sex hormone and growth factor dependent tumors or tumor components may be suppressed by lowering the levels of these factors in the patient's system. This does not however, deal with the problem of the remaining non-dependent tumors or tumor components. As shown by Fekete and others (supra), LHRH receptors are either present or appear in tumors and tumor components not dependent on sex hormone or growth factors.

Thus, LHRH analogs containing a cytotoxic moiety might serve as carriers for the chemotherapeutic agents. By binding to LHRH receptors without destroying the receptor site, such peptides could provide some target selectivity for the thus modified cytotoxic LHRH analog and make it "cell specific". After internalization, the cytotoxic component of these hybrid compounds could interfere with cellular events and thus cause cancer cell death.

There are several compounds among the clinically used anticancer drugs which have the potential of being coupled to a carrier peptide molecule. The coupling may be carried out through modification of the functional group of the cytotoxic moiety and/or the free amino- or carboxyl-group of a peptide.

The present invention deals with the provision of such LHRH analogs which possess high agonistic or antagonistic activity and contain cytotoxic side chains, such as moieties with quinone structure (naphthoquinones and anthraquinones substituted suitably by lower alkyl), alkylating agents, such as nitrogen mustards, moieties with three-membered rings, such as cyclopropyl, aziridinyl and epoxy, antitumor antibodies and antimetabolites like methotrexoyl. These LHRH analogs significantly inhibit the growth of different human breast cancer cell lines in cell cultures.

The compounds of this invention are represented by Formula I

wherein

R$^1$ is pGlu or D-Nal(2),

R$^2$ is His or D-Phe(4Cl),

R$^3$ is Trp, D-Trp or D-Pal(3),

R$^5$ is Tyr or Arg,

R$^6$ is D-Lys or D-Orn,

R$^{10}$ is Gly or D-Ala,

X is hydrogen or a lower alkanoyl group of 2–5 carbon atoms,

Q is a cytotoxic moiety having the formula

-continued

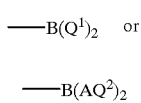

wherein

A is —NH—$(CH_2)_n$—CO— or —OC—$(CH_2)_n$—Co—
where n is 2–6,
B is —HN—$CH_2$—$(CH_2)_m$—CH(NH)—$(CH_2)_n$—CO—
where
m is 0 or 1,
n is 0 or 1,
the —CO moiety of A— and of B— being bonded to the epsilon or delta amino group or $R^6$ when $R^6$ is Lys or Orn respectively, and in the group $B(AQ^2)_2$, the —CO moiety of A— being bonded to an amino group on B,
$Q^1$ is D or L-Mel, cyclopropanecarbonyl, aziridine-2-carbonyl, epoxyalkyl or 1,4-aphthoquinone-5-oxycarbonyl-ethyl,
$Q^2$ is $Q^1$, 2-anthraquinonyl-methylenoxy or doxorubicinyl,
$Q^3$ is $Q^2$, mitomicinyl, esperamycinyl or methotrexoyl,
$Q^4$ is $Q^1$ or methotrexoyl and the pharmaceutically acceptable acid and base addition salts thereof.

The compounds of Formula I can be prepared by a combination of the solid phase technique and the classical (solution) synthesis.

Compounds of Formula I are preferably prepared from intermediate peptides of Formula VI:

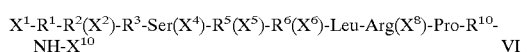

wherein
$R^1$, $R^2$, $R^3$, $R^5$, $R^6$ and $R^{10}$ are as defined above,
$X^1$ is an acyl group of 2–5 carbon atoms or provided that $R^1$ is pGlu, $X^1$ is hydrogen,
$X^2$ is a protecting group for His imidazole nitrogen,
$X^4$ is hydrogen or a protecting group for the Ser hydroxyl group,
$X^5$ is hydrogen or a protecting group for the Tyr phenolic hydroxyl group, or a protecting group for the guanidino group of Arg,
$X^6$ is hydrogen or a protecting group for the epsilon or delta amino group of $R^6$ when $R^6$ is Lys or Orn respectively,
$X^8$ is hydrogen or a protecting group for the Arg guanidino group,
$X^{10}$ is hydrogen or benzhydryl group incorporated into a resin.

Peptides of Formula VI are preferably synthesized by solid phase method.

Intermediate peptides of Formula VII can be obtained from peptides of Formula VI, wherein $X^2$, $X^4$, $X^5$, $X^6$, $X^8$, and $X^{10}$ are hydrogen, by acylation with A:

wherein $X^1$, $R^1$, $R^2$, $R^3$, $R^5$, $R^6$, $R^{10}$ and A are as defined above.

The acylation of peptides of Formula VI wherein $X^2$, $X^4$, $X^5$, $X^6$, $X^8$, and $X^{10}$ are hydrogen with suitably protected B gives after deprotection, intermediate peptides of Formula VIII:

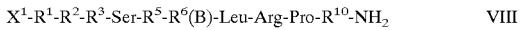

wherein $X^1$, $R^1$, $R^2$, $R^3$, $R^5$, $R^6$, $R^{10}$ and B are as defined above.

According to another suitable method, intermediate peptides of Formula VIII are obtained by deprotection of intermediate peptides of Formula VIIIA:

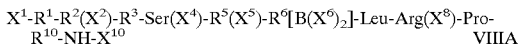

wherein $X^{6'}$ is hydrogen or a protecting group for the diaminoacid side chain, $R^1$, $R^2$, $R^3$, $R^5$, $R^6$, $R^{10}$, A, $X^1$, $X^2$, $X^4$, $X^5$, $X^6$, $X^8$, and $X^{10}$ are as defined above, which in turn are prepared by the solid phase method as intermediate peptides of Formula VI with the exception that suitably protected $R^6[B(X^6)_2]$ is incorporated in place of protected $R^6(X^6)$ in position 6.

To produce compounds of Formula I wherein Q is $B(Q^1)_2$, peptides of Formula VIII were reacted, for example, with an N-protected amino acid, an alkyl or an alkanoyl halide, for example Boc-D-or Boc-L-Mel, Trt-Azy, epibromohydrin, 5(3-chloropropionyloxy)-1,4-naphthoquinone or cyclopropanecarbonyl-chloride. Alternatively, compounds of Formula VI (wherein all X groups are H) with preformed $B(Q^1)_2$ wherein B and Q are as defined above.

To produce compounds of Formula I wherein Q is $B(AQ^2)_2$, peptides of Formula VIII were coupled with preformed $(AQ^2)$ wherein A and $Q^2$ are as defined above. Alternatively, compounds of Formula I wherein Q is $B(AQ^2)_2$, can be prepared by reacting peptides of Formula VIII first with an acylating agent with an A moiety and then, for example with Boc-D- or Boc-L-Mel, Trt-Azy, epibromohydrin, 2-hydroxymethyl-anthraquinone, hydroxymethylnaphthoquinone or Doxorubicin.

The synthesis of compounds of Formula I wherein Q is $A(Q^3)$ was carried out by first elongating the $R^6$ D-Lys or D-Orn side chain in peptides of Formula VI with a moiety of α,Ω-aminoalkanoic acid or α,Ω-dicarboxylic acid, forming peptides of Formula VII. For example, the peptide of Formula VI may be reacted with glutaric anhydride to yield a peptide where the A group is Glt. Next, the Formula VII peptide is coupled with for example, 2-hydroxymethyl-anthraquinone-, doxorubicin, mitomycin C, or methotrexate. Alternatively, compounds of Formula I wherein Q is $A(Q^3)$, can be prepared by reacting peptides of Formula VI where $X^6$=H with preformed $A(Q^3)$, where A and Q are as defined above.

The process of preparing compounds of Formula I wherein Q is $Q^4$ comprises reacting, for example, a peptide of Formula VI with D-Mel, Boc-D- or Boc-L-Mel, Trt-Azy, cyclopropanecarbonyl-chloride, epibromohydrin, 5(3-chloro-propionyloxy)1,4-naphthoquinone or methotrexate. Suitably, the reaction is carried out when $X^1$ is hydrogen or a lower alkanoyl group of 2–5 carbon atoms, and all other X moieties are hydrogen.

A pharmaceutical composition is provided by admixing the compound of Formula I with pharmaceutically acceptable carrier including microcapsules (microspheres) or microgranules (microparticles) formulated from poly(DL-lactide-co-glycolide) for sustained delivery.

DESCRIPTION OF THE PREFERRED EMBODIMENTS

For convenience in describing this invention, the conventional abbreviations for the amino acids, peptides and their derivatives are used as generally accepted in the peptide art and as recommended by the IUPAC-IUB Commission on Biochemical Nomenclature [European. J. Biochem., 138, 9–37 (1984)].

The abbreviations for the individual amino acid residues are based on the trivial name of the amino acid, e.g. pGlu is pyroglutamic acid, His is histidine, Trp is tryptophan, Ser is serine, Tyr is tyrosine, Lys is lysine, Orn is ornithine, Leu is leucine, Arg is arginine, Pro is proline, Gly is glycine, Ala is alanine and Phe is phenylalanine. Where the amino acid residue has isomeric forms, it is the L-form of the amino acid that is represented unless otherwise indicated.

Abbreviations of the uncommon amino acids employed in the present invention are as follows: D-Mel is 4-[bis(2-chloroethyl)amino]-D-phenylalanine, A$_2$pr is 2,3-diaminopropionic acid, D-Nal(2) is 3-(2-naphthyl)-D-alanine, D-Pal(3) is 3-(3-pyridyl)-D-alanine,D-Phe(4Cl) is 4-chloro-D-phenylalanine. Other abbreviations used are:

AcOH acetic acid
Ac$_2$O acetic anhydride
Ahx 6-aminohexanoyl
AQMO 2-anthraquinonyl-methylenoxy-, as represented by the structure

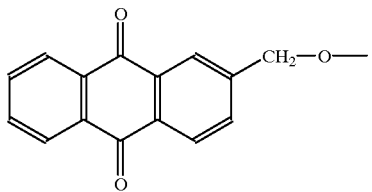

AQMOG 2-anthraquinonyl-methylenoxy-glutaryl-, as represented by the structure

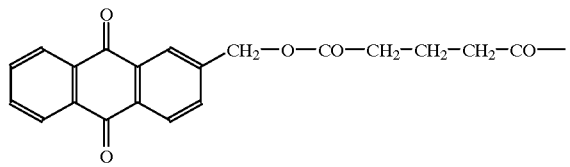

Azy aziridine-2-carbonyl
Boc tert.butoxycarbonyl
Bzl benzyl
CPC cyclopropanecarbonyl
DCB 2,6-dichlorobenzyl
DCC N,N'-dicyclohexylcarbodiimide
DCM dichloromethane
DIC N,N'-diisopropylcarbodiimide
DMF dimethylformamide
DOX doxorubicin (adriamycin)
EPP epoxy-propyl
ESP Esperamycin
Glt glutaryl, as represented by the structure —CO—CH$_2$—CH$_2$—CH$_2$—CO—
HOBt 1-hydroxybenzotriazole
HOPCP pentachlorophenol
HPLC high-performance liquid-chromatography
MeCN acetonitrile
MeOH methyl alcohol
MIT mitomycin C
MTX methotrexate (amethopterin)
NQCE 1,4-naphthoquinone-5-oxycarbonylethyl
TEA triethylamine
TFA trifluoroacetic acid
THF tetrahydrofuran
Tos 4-toluenesulfonyl
Z(2-Cl) 2-chloro-benzyloxycarbonyl
Z benzyloxycarbonyl Peptide sequences are written according to the convention whereby the N-terminal amino acid is on the left and the C-terminal amino acid is on the right.

In one especially preferred LHRH analog of Formula I $$X-R^1-R^2-R^3-Ser-R^5-R^6(Q)-Leu-Arg-Pro-R^{10}-NH_2 \qquad I$$

$R^1$ is D-Nal(2), $R^2$ is D-Phe(4Cl), $R^3$ is D-Trp or D-Pal (3), $R^5$ is Tyr or Arg, $R^6$ is D-lys, $R^{10}$ is D-Ala, and X is acetyl.

In another especially preferred LHRH analog of Formula I, $R^1$ is pGlu, $R^2$ is His, $R^3$ is Trp, $R^5$ is Tyr, $R^6$ is D-Lys or D-Orn, $R^{10}$ is Gly, and X is hydrogen.

In both of these preferred analogs, Q is a cytotoxic moiety having the formula:

$Q^4$ or $A(Q^3)$ or $B(Q^1)_2$ or $B(AQ^2)_2$ wherein
A is 6-aminohexanoyl or glutaryl residue
B is A$_2$pr,
$Q^1$ is D or L-Mel, cyclopropanecarbonyl, aziridine-2-carbonyl, epoxyalkyl or 1,4-naphthoquinone-5-oxycarbonyl-ethyl,
$Q^2$ is $Q^1$, 2-anthraquinonyl-methylenoxy or doxorubicinyl,
$Q^3$ is $Q^2$, mitomicin-C-yl, esperamycinyl or methotrexoyl, and
$Q^4$ is $Q^1$ or methotrexoyl.

The most particularly preferred embodiments are:
1. pGlu-His-Trp-Ser-Tyr-D-Lys(D-Mel)-Leu-Arg-Pro-Gly-NH$_2$
2. pGlu-His-Trp-Ser-Tyr-D-Lys(CPC)-Leu-Arg-Pro-Gly-NH$_2$
3. pGlu-His-Trp-Ser-Tyr-D-Lys(AQMOG)-Leu-Arg-Pro-Gly-NH$_2$
4. pGlu-His-Trp-Ser-Tyr-D-Lys(MTX)-Leu-Arg-Pro-Gly-NH$_2$
5. pGlu-His-Trp-Ser-Tyr-D-Lys[A$_2$pr(D-Mel)$_2$]-Leu-Arg-Pro-Gly-NH$_2$
6. pGlu-His-Trp-Ser-Tyr-D-Lys[A$_2$pr(CPC)$_2$]-Leu-Arg-Pro-Gly-NH$_2$
7. pGlu-His-Trp-Ser-Tyr-D-Lys[A$_2$pr(AQMOG)$_2$]-Leu-Arg-Pro-Gly-NH$_2$
8. pGlu-His-Trp-Ser-Tyr-D-Orn(D-Mel)-Leu-Arg-Pro-Gly-NH$_2$
9. pGlu-His-Trp-Ser-Tyr-D-Orn(CPC)-Leu-Arg-Pro-Gly-NH$_2$
10. pGlu-His-Trp-Ser-Tyr-D-Orn(AQMOG)-Leu-Arg-Pro-Gly-NH$_2$
11. pGlu-His-Trp-Ser-Tyr-D-Orn(MTX)-Leu-Arg-Pro-Gly-NH$_2$
12. pGlu-His-Trp-Ser-Tyr-D-Orn[A$_2$pr(D-Mel)$_2$]-Leu-Arg-Pro-Gly-NH$_2$
13. pGlu-His-Trp-Ser-Tyr-D-Orn[A$_2$pr(CPC)$_2$]-Leu-Arg-Pro-Gly-NH$_2$
14. pGlu-His-Trp-Ser-Tyr-D-Orn[A$_2$pr(AQMOG)$_2$]-Leu-Arg-Pro-Gly-NH$_2$
15. Ac-D-Nal(2)-D-Phe(4Cl)-D-Trp-Ser-Tyr-D-Lys(D-Mel)-Leu-Arg-Pro-D-Ala-NH$_2$
16. Ac-D-Nal(2)-D-Phe(4Cl)-D-Trp-Ser-Tyr-D-Lys(CPC)-Leu-Arg-Pro-D-Ala-NH$_2$
17. Ac-D-Nal(2)-D-Phe(4Cl)-D-Trp-Ser-Tyr-D-Lys (AQMOG)-Leu-Arg-Pro-D-Ala-NH$_2$
18. Ac-D-Nal(2)-D-Phe(4Cl)-D-Trp-Ser-Tyr-D-Lys(MTX)-Leu-Arg-Pro-D-Ala-NH$_2$
19. Ac-D-Nal(2)-D-Phe(4Cl)-D-Trp-Ser-Arg-D-Lys(D-Mel)-Leu-Arg-Pro-D-Ala-NH$_2$
20. Ac-D-Nal(2)-D-Phe(4Cl)-D-Trp-Ser-Arg-D-Lys(CPC)-Leu-Arg-Pro-D-Ala-NH$_2$ 21. Ac-D-Nal(2)-D-Phe(4Ci)-D-Trp-Ser-Arg-D-Lys(AQMOG)-Leu-Arg-Pro-D-Ala-NH$_2$
22. Ac-D-Nal(2)-D-Phe(4Cl)-D-Trp-Ser-Arg-D-Lys(MTX)-Leu-Arg-Pro-D-Ala-NH$_2$
23. Ac-D-Nal(2)-D-Phe(4Cl)-D-Trp-Ser-Arg-D-Lys[A$_2$pr(D-Mel)$_2$]-Leu-Arg-Pro-D-Ala-NH$_2$
24. Ac-D-Nal(2)-D-Phe(4Cl)-D-Trp-Ser-Arg-D-Lys[A$_2$pr(CPC)$_2$]-Leu-Arg-Pro-D-Ala-NH$_2$
25. Ac-D-Nal(2)-D-Phe(4Cl)-D-Trp-Ser-Arg-D-Lys[A$_2$pr(AQMOG)$_2$]-Leu-Arg-Pro-D-Ala-NH$_2$
26. Ac-D-Nal(2)-D-Phe(4Cl)-D-Pal(3)-Ser-Arg-D-Lys(D-Mel)-Leu-Arg-Pro-D-Ala-NH$_2$
27. Ac-D-Nal(2)-D-Phe(4Cl)-D-Pal(3)-Ser-Arg-D-Lys(CPC)-Leu-Arg-Pro-D-Ala-NH$_2$
28. Ac-D-Nal(2)-D-Phe(4Cl)-D-Pal(3)-Ser-Arg-D-Lys(AQMOG)-Leu-Arg-Pro-D-Ala-NH$_2$
29. Ac-D-Nal(2)-D-Phe(4Cl)-D-Pal(3)-Ser-Arg-D-Lys(MTX)-Leu-Arg-Pro-D-Ala-NH$_2$
30. Ac-D-Nal(2)-D-Phe(4Cl)-D-Pal(3)-Ser-Arg-D-Lys[A$_2$pr(D-Mel)$_2$]-Leu-Arg-Pro-D-Ala-NH$_2$
31. Ac-D-Nal(2)-D-Phe(4Cl)-D-Pal(3)-Ser-Arg-D-Lys[A$_2$pr(CPC)$_2$]-Leu-Arg-Pro-D-Ala-NH$_2$
32. Ac-D-Nal(2)-D-Phe(4Cl)-D-Pal(3)-Ser-Arg-D-Lys[A$_2$pr(AQMOG)$_2$]-Leu-Arg-Pro-D-Ala-NH$_2$
33. pGlu-His-Trp-Ser-Tyr-D-Lys(Glt-DOX)-Leu-Arg-Pro-Gly-NH$_2$
34. pGlu-His-Trp-Ser-Tyr-D-Lys[Ahx(MTX)]-Leu-Arg-Pro-Gly-NH$_2$ The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartrate, and the like.

Microcapsules or microparticles of these peptides formulated from poly(DL-lactide-co-glycolide) may be the preferred sustained delivery systems. Intravenous administration in isotonic saline, phosphate buffer solutions or the like may be also used.

The pharmaceutical compositions will usually contain the peptide in conjunction with a conventional, pharmaceutically-acceptable carrier. Usually, the dosage will be from about 1 to about 100 µg of the peptide per kilogram of the body weight of the host when given intravenously. Overall, treatment of subjects with these peptides is generally carried out in the same manner as the clinical treatment using other agonists and antagonists of LHRH. Thus, greater dosage levels of the peptide may be administered when it is felt delivery of greater cytotoxin levels is desirable.

These peptides can be administered to mammals intravenously, subcutaneously, intramuscularly, intranasally or intravaginally to achieve antitumor effect. Effective dosages will vary with the form of administration and the particular species of mammal being treated. An example of one typical dosage form is a physiological saline solution containing the peptide which solution is administered to provide a dose in the range of about 1 to 25 µg/kg of body weight.

Assay Procedures

The compounds of this invention exhibit powerful effect on gonadotropin release by the pituitary, bind to tumor cell membranes and inhibit [$^3$H]thymidine incorporation into DNA in cell cultures.

(a) LH-releasing and LH-RH-inhibiting activities

Ability of compounds to influence LH release in vitro is assayed by using a superfused rat pituitary cell system [S. Vigh and A. V. Schally, Peptides, 5 Suppl. 1, 241–247 (1984); V. Csernus and A. V. Schally, in Neuroendocrine Research Methods, Ed. B. Greenstein, Harwood Academic Publishers, London, (1990)].

LH-releasing effect of compounds is determined as follows: each peptide is perfused through the cells for 3 min (1 ml perfusate) at 20–100 pM. LH content of 1 ml fractions collected is determined by radioimmunoassay (RIA). Potency of peptides is compared to that of 3 nM LHRH perfused similarly.

LHRH inhibiting effect of peptides is assayed as follows: each peptide is perfused through the cells for 9 min (3 ml perfusate) at 1 nM. Immediately after that, a mixture containing the same concentration of peptide and 3 nM LHRH is administered for 3 min. This was followed by four consecutive infusions of 3 nM LHRH for 3 min (1 ml perfusate) at 30 min intervals (30, 60, 90, 120 min). LH content of the 1 ml fractions collected is determined by RIA.

(b) In vivo Antiovulatory Activity

This activity of the peptides is determined in 4-day-cycling rats as described [A. Corbin and C. W. Beattie, Endocr. Res. Commun., 2, 1–23 (1975)].

(c) Receptor Binding.

Affinity for peptides to human breast cancer cell membranes is determined by using labelled LHRH and [D-Trp$^6$] LHRH. The assay is carried out similarly to that described by T. Kadar et al., Proc. Natl. Acad. Sci. USA, 85, 890–894 (1988) and M. Fekete et al., Endocrinology, 124, 946–955 (1989).

(d) Cytotoxicity Test.

Ability of peptides of Formula I to inhibit incorporation of [$^3$H]thymidine into DNA of monolayer cultures the human mammary tumor cell line MCF-7 is assayed as described [V. K. Sondak et al., Cancer Research, 44, 1725–1728 (1984); F. Holzel et al., J. Cancer Res. Clin. Oncol. 109, 217–226 (1985); M. Albert et al., J. Cancer Res. Clin. Oncol. 109, 210–216 (1985)].

Synthesis of Peptides

The peptides of the present invention may be prepared by any techniques that are known to those skilled in the peptide art. A summary of the techniques so available may be found in M. Bodanszky, Principles of Peptide Synthesis, Springer-Verlag, Heidelberg, 1984. Classical solution synthesis is described in detail in the treatise "Methoden der Organische Chemie" (Houben-Weyl), Vol. 15, Synthese von Peptiden, Parts I and II, Georg Thieme Verlag, Stuttgart, 1974. The techniques of exclusively solid-phase synthesis are set forth in the textbook of J. M. Stewart and J. D. Young, Solid Phase Peptide Synthesis, Pierce Chem Co., Rockford, Ill., 1984 (2nd ed.) and in the review of G. Barany, et al., Int. J. Peptide Protein Res. 30, 705–739, 1987.

The basic peptides of this invention were synthesized by solid-phase method, and only the cytotoxic side chains were incorporated by "classical" procedure. In the solid phase synthesis, suitable protected amino acids (sometimes protected peptides) are added stepwise in C→N direction once the C-terminal amino acid has been appropriately attached (anchored) to an inert solid support (resin). After completion of a coupling step, the N-terminal protecting group is removed from this newly added amino acid residue and the next amino acid (suitably protected) is then added, and so forth, After all the desired amino acids have been linked in the proper sequence, the peptide is cleaved from the support and freed from the remaining protecting group(s) under conditions that are minimally destructive towards residues in the sequence. This must be followed by a prudent purification and scrupulous characterization of the synthetic product, so as to ensure that the desired structure is indeed the one obtained.

Preferred Embodiment of Synthesis

A particularly preferred method of preparing compounds of the present invention is the solid phase synthesis; the incorporations of cytotoxic side chains are performed in solution. The peptides of Formula I wherein $R^6$ is D-Lys or D-Orn are preferably prepared from intermediate peptides of Formula VI:

$$X^1\text{-}R^1\text{-}R^2(X^2)\text{-}R^3\text{-}Ser(X^4)\text{-}R^5(X^5)\text{-}R^6(X^6)\text{-}Leu\text{-}Arg(X^8)\text{-}Pro\text{-}R^{10}\text{-}NH\text{-}X^{10} \qquad VI$$

wherein $R^1$, $R^2$, $R^3$, $R^5$, $R^6$, $R^{10}$ and $X^1$ are as defined hereinabove, $X^2$ is p-toluenesulfonyl or 2,4-dinitrophenyl protecting group if $R^2$ is His or H if $R^2$ is D-Phe(4Cl), $X^4$ is a protecting group for the hydroxyl group of serine, such as benzyl (Bzl)—the preferred group—or 2,6-dichlorobenzyl (DCB), $X^5$ is benzyl, 2-Br-benzyloxycarbonyl or DCB (preferred) for protecting the phenolic hydroxyl where $R^5$ is Tyr, or is Tos (preferred), nitro or methyl-(t-butylbenzene)-sulfonyl to protect the guanidino group if $R^5$ is Arg, $X^6$ is a protecting group for the epsilon or delta amino group or $R^6$ for Lys or Orn respectively, such as Z, Z(2-Cl) (preferred), $X^8$ is a protecting group for Arg, such as nitro, methyl-(t-butylbenzene)-sulfonyl or Tos (preferred), and $X^{10}$ is an amide protecting benzhydryl or methylbenzhydryl group incorporated into resin support. For synthesis of peptide amides, the commercially available benzhydrylamino-polystyrene-2% divinylbenzene copolymer is preferred.

The solid phase synthesis of the peptides of Formula VI is commenced by the attachment of Boc-protected Gly or D-Ala to a benzhydrylamine resin in $CH_2Cl_2$. The coupling is carried out using DIC or DIC/HOBt at ambient temperature. After the removal of the Boc group, the coupling of successive protected amino acids (each is applied in a 3 molar excess) is carried out in $CH_2Cl_2$ or in mixtures of DMF/$CH_2Cl_2$ depending on the solubility of Boc-amino acids. The success of the coupling reaction at each stage of the synthesis is preferably monitored by the ninhydrin test as described by Kaiser et al. [Anal. Biochem. 34, 595 (1970)]. In cases where incomplete coupling occurs, the coupling procedure is repeated before removal of the alpha-amino protecting group prior to the reaction with the next amino acid.

After the desired amino acid sequence of intermediate peptides of Formula VI has been completed, if desired, the N-terminal acetylation is carried out using $Ac_2O$/imidazole, and the peptide-resin is then treated with liquid HF in the presence of anisole to yield the peptides of Formula VI wherein $X^2$, $X^4$, $X^5$, $X^6$, $X^8$, and $X^{10}$ are hydrogen.

Acylation of peptides of Formula VI with glutaric anhydride or coupling with Boc-6-aminohexanoic acid, followed by deprotection gives peptides of Formula VI:

$$X^1\text{-}R^1\text{-}R^2\text{-}R^3\text{-}Ser\text{-}R^5\text{-}R^6(A)\text{-}Leu\text{-}Arg\text{-}Pro\text{-}R^{10}\text{-}NH_2 \qquad VII$$

wherein $X^1$, $R^1$, $R^2$, $R^3$, $R^5$, $R^6$, and $R^{10}$ are as defined above, and A is glutaryl or 6-aminohexanoyl.

Acylation of peptides of structure of Formula VI with an appropriate Boc-protected diamino alkanoic acid, suitably 2,3-diamino propionic acid, after deprotection gives the peptides of Formula VIII:

$$X^1\text{-}R^1\text{-}R^2\text{-}R^3\text{-}Ser\text{-}R^5\text{-}R^6(B)\text{-}Leu\text{-}Arg\text{-}Pro\text{-}R^{10}\text{-}NH_2 \qquad VIII$$

wherein $X^1$, $R^1$, $R^2$, $R^3$, $R^5$, $R^6$, and $R^{10}$ are as defined hereinabove, and B is diamino alkanoyl, suitably 2,3-diamino propionyl.

In an alternate synthesis, peptides of Formula VIII are obtained by deprotection of intermediate peptides of Formula VIIIA which are prepared by the solid phase method exactly as peptides having the Formula VI, but a suitably protected $R^6(B)$ residue, preferably Boc-$R^6[B(Z)_2]$, is incorporated in position 6 instead of Boc-$R^6(X^6)$.

Compounds of Formula I wherein residue Q is $B(Q^1)_2$ are prepared from intermediate peptides of Formula VIII by acylating with Boc-D- or Boc-L-Mel-OPCP or Trt-Azy. Alternatively, cyclopropane alkanoyl halides, suitably cyclopropane carbonyl chloride are used to obtain $(CPC)_2$ containing analogs; or alkylation of peptides of Formula VIII with epibromohydrin or 5(3-chloropropionyloxy)-1,-4-naphthoquinone gives $(EPP)_2$ or $(NQCE)_2$ containing analogs.

Alternatively, compounds of Formula I wherein Q is $B(Q^1)_2$ may be prepared by coupling peptides of Formula VI with preformed $B(Q^1)_2$ wherein B and $Q^1$ are as defined above, for example by the carbodiimide reaction.

Compounds of Formula I wherein residue Q is $B(AQ^2)_2$ are preferably prepared from intermediate peptides of Formula VIII, coupling the $B(AQ^2)_2$ and intermediate peptide to form the compound. Where $AQ^2$ is AQMOG (i.e., 2-anthraquinonyl-methylenoxy-glutaryl), the intermediate peptide of Formula VIII is coupled to 2-anthraquinonyl-methylenoxy hemiglutarate in the carboduimide reaction.

To produce compounds of Formula I wherein Q is $A(Q^3)$, mitomycin C, MTX or doxorubicin are bound to intermediate peptides of Formula VII by carbodiumide reaction. Where instead one desires a compound wherein Q is AQMOG or ESP, different groups of peptides of Formula I may be formed by coupling a preformed $A(Q^3)$ (in the form of 2-anthraquinonyl-methylenoxy hemiglutarate or hemiglutaryl-esperamycin respectively) with peptides of Formula VI by the carbodiimide reaction.

Peptides of Formula VI are converted into peptides of Formula I wherein Q is $Q^4$ by carbodiimide coupling with 1.1 equivalent of Trt-Azy, or MTX or instead reacting Formula VI peptides with Boc-D- or Boc-L-Mel-OPCP. Peptides of Formula VI were acylated with cyclopropanecarbonyl-chloride to obtain analogs with CPC moiety. Alkylation of peptides of Formula I with epibromohydrin or 5(3-chloropropionyloxy)1-4-naphthoquinone give EPP- or NQCE-containing analogs.

Although the invention has been described with regard to its preferred embodiments, it should be understood that changes and modifications obvious to one having the ordinary skill in this art may be made without departing from the scope of the invention, which is set forth in the claims which are appended thereto. Substitutions known in the art which do not significantly detract from its effectiveness may be employed in the invention.

PURIFICATION OF PEPTIDES

Crude synthetic products (>500 mg) were purified on a BECKMAN Prep-350 preparative HPLC system equipped with a DYNAMAX MACRO column (41.4×250 mm)

packed with spherical C18 silica gel (pore size: 300 Å, particle size: 12 µm) (RAININ Inc., Co., Woburn, Mass.) (Column A). Purification of smaller amount of peptides (<250 mg) were performed on a BECKMAN HPLC system (Model 142) using a DYNAMAX MACRO (21.2×250 mm) column packed with the same medium, as above (Column B). To purify peptides weighing <50 mg, a reversed phase, 10×250 mm VYDAC Protein & Peptide $C_{18}$ column (pore size: 300 Å, particle size: 5 µm) (ALTECH, Deerfield, Ill.) (Column C) or a 10×250 mm W-POREX $C_{18}$ column (pore size: 300 Å, particle size: µm) (Phenomenex, Rancho Palos Verdes, Calif.) (Column D) were used. Columns were eluted with solvent system i consisting of (A) 0.10% aqueous TFA and (B) 0.10% TFA in 70% aqueous acetonitrile or solvent system ii consisting of (A) 0.2% aqueous acetic acid and (B) 0.2% acetic acid in 70% aqueous acetonitrile usually in a gradient mode. Column eluant was monitored with UV detectors operating at 230 or 280 nm. Chromatography was effected at ambient temperature.

ANALYTICAL HPLC

Analysis of crude and purified peptides was carried out with a Hewlett-Packard Model 1090 liquid chromatograph equipped with a diode array detector set at 220 and 280 nm and a reversed phase 4.6×250 mm W-POREX $C_{18}$ column (pore size: 300 Å, particle size: 5 µm) (Column E). A flow rate of 1.2 ml/min of solvent system i was maintained and the separations were performed at room temperature.

AMINO ACID ANALYSIS

Peptide samples were hydrolyzed at 110° C. for 20 hr in evacuated sealed tubes containing 4 M methane-sulfonic acid. Analyses were performed with a Beckman 6300 amino acid analyzer.

PREPARATION I

Boc-D-Mel-OPCP

D-4-[bis-(2-chloroethyl)amino]phenylalanine, D-Mel, (5 mmol) was converted to its Boc derivative as described for the L isomer [H. Kun-hwa and G. R. Marshall, J. Med. Chem. 24, 1304–1310 (1981)] with the exception that di-tert-butyl dicarbonate was used as acylating agent instead of Boc-azide. The oily product, Boc-D-Mel, was dissolved in THF (10 ml) and cooled to 0° C. To the stirred solution pentachlorophenol (5.25 mmol) and DIC (6.5 mmol) were added. After 10-min. stirring, the reaction mixture was filtered, the cake was washed with THF (2×5 ml) and the filtrate was evaporated to a small volume (5 ml). 10 ml of ethanol was added and the crystals were separated after 2 hours cooling (0° C.). Boc-D-Mel-OPCP thus obtained (about 3.4 mmol) had a m.p. of 138–140° C.

PREPARATION II pGlu-His-Trp-Ser-Tyr-D-Lys-Leu-Arg-Pro-Gly-NH$_2$ (IIA) and pGlu-His-Trp-Ser-Tyr-D-Orn-Leu-Arg-Pro-Gly-NH$_2$ (IIB)

[D-Lys]$^6$LHRH [N. C. Nicholas et al., J. Med. Chem., 19 937–941 (1976)] and [D-Orn]$^6$LHRH were built step by step on a benzhydrylamine HCl resin containing about 1 meq NH$_2$/g (Advanced ChemTech, Louisville, Ky.) in a reaction vessel for manual solid-phase synthesis starting with Boc-Gly in accordance with the procedures set forth below.

The benzhydrylamine HCl resin (1 g, about 1 mmol), after neutralization with 10% TEA in CH$_2$Cl$_2$, was coupled sequentially with a 3 molar excess of protected amino acids in accordance with the Schedule as follows:

| STEP | REAGENTS AND OPERATIONS | MIXING TIMES (min) |
|---|---|---|
| 1 | Coupling: Boc-amino acid in DCM or DMF depending on the solubility of the particular protected amino acid, plus DIC | 60–90 |
| 2 | MeOH (or DMF then MeOH) wash | 2 |
| 3 | DCM wash | 2 |
| 4 | MeOH wash | 2 |
| 5 | DCM wash (three times) | 2 |
| 6 | Deprotection: 50% TFA in DCM (twice) | 5 and 25 |
| 7 | DCM wash | 2 |
| 8 | 2-Propanol wash | 1 |
| 9 | Neutralization: 10% TEA in DCM | 2 |
| 10 | MeOH wash | 1 |
| 11 | Neutralization: 10% TEA in DCM | 2 |
| 12 | MeOH wash | 1 |
| 13 | DCM wash (three times) | 2 |

Thus, the resin was treated with Boc-Gly, Boc-Pro, Boc-Arg(Tos), Boc-Leu, Boc-D-Lys[Z(2-Cl)], Boc-Tyr(Bzl), Boc-Ser(Bzl), Boc-Trp, Boc-His(Tos), and pGlu during successive coupling cycles to yield a peptide-resin with structure of pGlu-His(Tos)-Trp-Ser(Bzl)-Tyr(DCB)-D-Lys[Z(2-Cl)]-Leu-Arg(Tos)-Pro-Gly-NH-RESIN. Using Boc-D-Orn (Z) instead of Boc-D-Lys[Z(2-Cl)] leads to the peptide resin having the structure of pGlu-His(Tos)-Trp-Ser(Bzl)-Tyr(DCB)-D-Orn(Z)-Leu-Arg(Tos)-Pro-Gly-NH-RESIN.

The peptide-resins thus obtained were treated with 2 ml anisole and 20 ml of HF at 0° for 45 min. After elimination of HF under vacuum, the peptide-resin remainder was washed with dry diethyl ether. The peptide was then extracted with 50% aqueous acetic acid, separated from the resin by filtration, and lyophilized.

Crude peptides (860 mg, 725 mg) were purified on Column A with solvent system i using a linear gradient of 10–40% B in 60 min at flow rate of 30 ml/min. 230 nm.

Purified peptides proved to be substantially (>96%) pure in analytical HPLC by using solvent system i in a linear gradient mode (15–35% B in 20 min). Retention times are 11.3 min and 10.4 min, respectively. Amino acid analysis gave the expected results.

PREPARATION III pGlu-His-Trp-Ser-Tyr-D-Lys(A$_2$pr)-Leu-Arg-Pro-Gly-NH$_2$(IIIA) and pGlu-His-Trp-Ser-Tyr-D-Orn(A$_2$pr)-Leu-Arg-Pro-Gly-NH$_2$(IIIB)

A solution of Boc$_2$A$_2$pr (60.6 mg) in DMF (1 ml) was cooled to 0° C., pentachlorophenol (60 mg) and 35 µl DIC were added and the mixture was stirred for one hour. [D-Lys]$^6$LHRH (319 mg of the TFA salt) in DMF (0.5 ml) was neutralized with TEA (84 µl) and poured into the above prepared active ester solution. The reaction mixture was allowed to stir for 2 hours at 0° C. After concentrating under vacuum, the oily residue was dissolved in 0.1% TFA and diethyl ether and the aqueous phase was subjected to HPLC on Column B with solvent system i in a linear gradient mode (20–60% solvent B in 60 min). The pure Boc-protected peptide was then treated with 30% TFA in DCM to yield the TFA salt of [D-Lys(A$_2$pr)$^6$]LHRH (IIIA) (251 mg).

Proceeding in a similar manner but using TFA salts of [D-Orn]⁶LHRH as starting material gave Preparation IIIB (202 mg).

HPLC retention times for peptides IIIA and IIIB were 12.2 min and 11.2 min using solvent system i in a linear gradient mode (15–35% B in 20 min).

PREPARATION IV

Ac-D-Nal(2)-D-Phe(4Cl)-D-Trp-Ser-Arg-D-Lys-Leu-Arg-Pro-D-Ala-NH$_2$ (IV)

The preparation of IV was carried out by solid-phase method in accordance with the procedures set forth in the Schedule of Preparation II. The synthesis was commenced by coupling Boc-D-Ala to 1 g benzhydrylamine resin containing about 1.0 meq NH$_2$. The decapeptide was built up in nine successive coupling steps using Boc-Pro, Boc-Leu, Boc-Arg(Tos), Boc-Lys[Z(2-Cl)], Boc-Tyr(DCB), Boc-Ser (Bzl), Boc-Trp, Boc-D-Phe(4Cl), Boc-D-Nal(2). N-Terminal acetylation was performed with a 50-fold excess of acetic anhydride in CH$_2$Cl$_2$ for 30 min. The peptide was cleaved from the resin with 15 ml of HF in the presence of 1.5 ml m-cresol at 0° C. for 30 min and at room temperature for 30 min. After elimination of HF, the mixture of resin and peptide was washed with diethyl ether, the peptide was extracted with DMF. The DMF solution was concentrated to a small volume under high vacuum, then triturated with diethylether. The crude product thus obtained was purified by preparative HPLC as described for Preparation II, using a linear gradient of 40–70% B in 60 min. The pure peptide (837 mg) has a retention time of 25.5 min using solvent system i in a linear gradient mode (30–60% B in 30 min).

PREPARATION V

Ac-D-Nal(2)-D-Phe(4Cl)-D-Pal(3)-Ser-Arg-D-Lys-Leu-Arg-Pro-D-Ala-NH$_2$ (VA)

Ac-D-Nal(2)-D-Phe(4Cl)-D-Trp-Ser-Arg-D-Lys-Leu-Arg-Pro-D-Ala-NH$_2$ (VB)

The peptides of VA and VB were prepared by the solid-phase technique on a benzhydrylamine HCl resin in accordance with the procedures set forth in the Schedule of Preparation II.

Thus, the resin (0.5 g containing about 0.5 mmole NH$_2$) was treated during the ten successive coupling cycles with Boc-D-Ala, Boc-Pro, Boc-Leu, Boc-Arg(Tos), Boc-Lys[Z (2-Cl)], Boc-Arg(Tos), Boc-Ser(Bzl), Boc-D-Pal(3), Boc-D-Phe(4Cl), Boc-D-Nal(2) and finally with Ac$_2$O/imidazole to yield a peptide-resin which was then treated with HF and anisole to afford the free, D-Lys-containing decapeptide of VA (540 mg).

Proceeding in a similar manner but incorporating Boc-D-Trp in place of Boc-D-Pal(3) at position 3, the free, D-Lys-containing decapeptide of VB was prepared (500 mg). Peptides were purified on Column A with a gradient of solvent system i (20–60% B in 80 min). HPLC retention times of VA and VB and are 11.4 min and 18.8 min, respectively, when using solvent system i in a linear gradient mode (30–50% B in min).

PREPARATION VI

Boc-D-Lys(Z$_2$-A$_2$pr)

To a mixed anhydride prepared from Z$_2$-A$_2$pr (0.72 g) and ethyl chloroformate (0.2 ml) in the presence of TEA (0.28 ml) in DMF solution (4 ml), Boc-D-Lys (0.5 g) and TEA (0.3 ml) in 50% aqueous DMF (4 ml) were added with stirring at 0° C. After 2 hours stirring at 0° C., the reaction mixture was concentrated to an oil under reduced pressure, dissolved in water and ethyl acetate, acidified with 1 M KHSO$_4$. The organic phase was washed with water, then dried over Na$_2$SO$_4$ and evaporated under vacuum to yield Boc-D-Lys (Z$_2$-A$_2$pr) (1.1 g).

PREPARATION VII

Ac-D-Nal(2)-D-Phe(4Cl)-D-Pal(3)-Ser-Arg-D-Lys (A$_2$pr)-Leu-Arg-Pro-D-Ala-NH$_2$ (VIIA)

Ac-D-Nal(2)-D-Phe(4Cl)-D-Trp-Ser-Arg-D-Lys (A$_2$pr)-Leu-Arg-Pro-D-Ala-NH$_2$ (VIIB)

Compounds VIIA and VIIB were built step by step on a benzhydrylamine HCl resin containing about 1 meq NH$_2$/g (Advanced ChemTech, Louisville, Ky.) in a reaction vessel for manual solid-phase synthesis starting with Boc-D-Ala in accordance with the procedures set forth below.

The benzhydrylamine HCl resin (1 g, about 1 mmol), after neutralization with 10% TEA in CH$_2$Cl$_2$, was coupled sequentially with 3 molar excess of protected amino acids in accordance with the Schedule given in Preparation II.

Thus, the resin was treated with Boc-D-Ala, Boc-Pro, Boc-Arg(Tos), Boc-Leu, Boc-D-Lys(Z$_2$-A$_2$pr) (Preparation VI), Boc-Arg(Tos)), Boc-Ser(Bzl), Boc-D-Pal(3), Boc-D-Phe(4Cl), and Boc-D-Nal(2). After the amino acid sequence of the decapeptide had been completed, the terminal Boc group was removed and the N-terminal was acetylated by using 10-fold excess of Ac$_2$O and imidazole to yield the peptide-resin with the structure of Ac-D-Nal(2)-D-Phe(4Cl)-D-Pal(3)-Ser(Bzl)-Arg(Tos)-D-Lys(Z$_2$-A$_2$pr)-Leu-Arg (Tos)-Pro-D-Ala-NH-RESIN. Proceeding in a similar manner but incorporating Boc D-Trp in place of Boc-D-Pal(3), the peptide-resin with the structure of Ac-D-Nal(2)-D Phe (4Cl)-D-Trp-Ser(Bzl)-Arg(Tos)-D-Lys(Z$_2$A$_2$pr)-Leu-Arg (Tos)-Pro-D-Ala-RESIN was prepared.

The peptide-resin thus obtained was treated with anisole and HF, and the crude free peptides were isolated as described in Preparation IV. Thereafter the crude peptides (1.3 g) are subjected to purification by HPLC on Column A using solvent system i in a linear gradient mode (20–50% B in 60 min).

Peptides VIIA and VIIB thus obtained (705 mg and 780 mg) were judged to be substantially (>95%) pure by using solvent system i in a linear gradient mode (30–50% B in 20 min). Retention times are 10.1 min and 17.5 min, respectively.

Alternatively, Preparation VIIA and VIIB were obtained from Preparation VA and VB by acylation with Boc$_2$-A$_2$pr as described at Preparation III. After purification, the Boc-protected peptides were treated with 50% TFA in DCM and repurified by HPLC (see above).

PREPARATION VIII pGlu-His-Trp-Ser-Tyr-D-Lys(Ahx)-Leu-Arg-Pro-Gly-NH$_2$ 160 mg of [D-Lys]⁶LHRH was dissolved in DMF (0.5 ml), neutralized with 3 eq TEA (42 μl),then Boc-Ahx (28 mg), DIC (20 μl), and HOBt (19 mg) is added and stirred at 0° C. for 2 hours. The Boc-protected peptide was isolated by precipitating with diethyl-ether and purification by HPLC on Column B with a gradient of solvent system i (20–50% B in 60 min). Fractions containing protected peptide were treated with 30% TFA in DCM. Repurification on Column B using solvent system i in gradient mode (10–30% B in 40 min) yielded 79 mg of [D-Lys-Ahx]⁶LHRH. HPLC retention time for Preparation VIII was 9.0 min when using solvent system i in a linear gradient mode (20–40% B in 20 min).

PREPARATION IX pGlu-His-Trp-Ser-Tyr-D-Lys(Glt)-Leu-Arg-Pro-Gly-NH$_2$

The peptide IX was prepared by acylation of [D-Lys]⁶LHRH (Preparation IIIA, 160 mg) with glutaric anhydride (57 mg) in 500 μl DMF in the presence of TEA (42 μl) for 2 hours at room temperature. The crude [D-Lys(Glt)]⁶LHRH was purified by HPLC on Column B using solvent system i in gradient mode (20–40% B in 40 min). The pure Preparation IX (120 mg) had a HPLC retention time 12.4 min when using solvent system i in linear gradient mode (20–40% B in 20 min).

PREPARATION X 2-anthraquinonyl-methylenoxy hemiglutarate 576 mg (2 mmol) of 2-hydroxymethyl-anthraquinone was suspended in 6 ml of anhydrous pyridine and was refluxed for 24 hours with 456 mg (4 mmol) glutaric anhydride. Pyridine was eliminated under vacuum, the residue is acidified and extracted with ethyl acetate. The yellow product was recrystallized from ethyl acetate-hexane (580 mg, m.p.: 150–151 ° C.). HPLC retention time of Preparation VIII is 19.7 min using solvent system i (linear gradient of 30–60% B in 30 min).

PREPARATION XI

5(3-Chloro-propionyloxy)-1,4-naphthoquinone

A solution of triethylamine (1.4 ml) and 1.27 g. of 3-chloropropionylchloride in 5 ml. of DCNM was added to a solution of 1.73 g. of 5-hydroxy-1,4-naphthoquinone. The reaction mixture was stirred for 2 hours at room temperature. The solution was filtered and concentrated to a small volume and chromatographed on a silica gel column (ethylacetate-cyclohexane-DCM) to give 741 mg. of desired product.

EXAMPLE I pGlu-His-Trp-Ser-Tyr-D-Lys(D-Mel)-Leu-Arg-Pro-Gly-NH$_2$ (1)

The peptide pGlu-His-Trp-Ser-Tyr-D-Lys(D-Mel)-Leu-Arg-Pro-Gly-NH$_2$ (1) was prepared by reacting [D-Lys]⁶LHRH (Preparation IIA, 31.9 mg (20 μmol) of the TFA salt) in 0.5 ml of DMF with Boc-D-Mel-OPCP (Preparation I, 26 mg) in 200 μl of MeCN in the presence of 4 meq of TEA. The mixture was continuously stirred for 10 hours at room temperature. The reaction mixture was precipitated with diethylether, filtered and washed with the same solvent for three times. The Boc-protected peptide thus obtained was treated with 5.0 ml of 50% TFA in CH$_2$Cl$_2$ for 10 min at room temperature, evaporated and subjected to HPLC on Column C using solvent system ii. Lyophilized fractions containing pure peptide yielded 14.3 mg of 1.

Peptides pGlu-His-Trp-Ser-Tyr-D-Orn(D-Mel)-Leu-Arg-Pro-Gly-NH$_2$ (8) (15.1 mg), [Ac-D-Nal(2)-D-Phe(4Cl)-D-Trp-Ser-Tyr-D-Lys(D-Mel)-Leu-Arg-Pro-D-Ala-NH$_2$ (15) (16 mg), [Ac-D-Nal(2)-D-Phe(4Cl)-D-Trp-Ser-Arg-D-Lys(D-Mel)-Leu-Arg-Pro-D-Ala-NH$_2$ (19) (13.6 mg), [Ac-D-Nal(2)-D-Phe(4Cl)-D-Pal(3)-Ser-Arg-D-Lys(D-Mel)-Leu-Arg-Pro-D-Ala-NH$_2$ (26) (12.1 mg) were obtained in a similar manner but using [D-Orn]⁶LHRH (Preparation IIB, 31.6 mg), [Ac-D-Nal(2)¹,D-Phe(4Cl)², D-Trp³, D-Lys⁶,D-Ala¹⁰]LHRH (Preparation IV,33.4 mg), [Ac-D-Nal(2)¹,D-Phe(4Cl)², D-Trp³,Arg⁵, D-Lys⁶, D-Ala¹⁰]LHRH (Preparation VA, 35.6 mg) and [Ac-D-Nal(2)¹,D-Phe(4Cl)², D-Pal(3)³,Arg⁵,D-Lys⁶,D-Ala¹⁰]LHRH (Preparation VB, 34.8 mg), respectively.

| Peptide No. | HPLC data Gradient (% B/min) for | | Retention time (Min) |
|---|---|---|---|
| | Purification | Analysis | |
| 01 | 20–50/60 | 35–55/20 | 8.8 |
| 08 | 20–50/60 | 35–55/20 | 7.8 |
| 15 | 40–70/60 | 65–85/20 | 11.5 |
| 19 | 35–55/40 | 50–70/20 | 11.2 |
| 26 | 30–50/40 | 40–60/20 | 13.5 |

EXAMPLE II pGlu-His-Trp-Ser-Tyr-D-Lys(CPC)-Leu-Arg-Pro-Gly-NH$_2$ (2)

Preparation of pGlu-His-Trp-Ser-Tyr-D-Lys(CPC)-Leu-Arg-Pro-Gly-NH$_2$ (2) was achieved in an acylation reaction of [D-Lys]⁶LHRH (Preparation IIA, 31.9 mg of the TFA salt) with cyclopropane-carbonylchloride. The peptide was dissolved in 0.2 ml of DMF, neutralized with addition of TEA and cooled down to −30° C. 10 μl (umol) of 20% solution of cyclopropanecarbonylchloride in MeCN is given. This process was repeated two times and the reaction mixture was kept at 0° C. over-night. The reaction mixture was diluted with a little amount of water and was injected onto Column C to purify in solvent system i. Lyophilized fractions containing pure peptide yielded 8.3 mg of 2.

Proceeding in a similar manner but using [D-Orn]⁶LHRH (Preparation IIB, 31.6 mg), [Ac-D-Nal(2)¹,D-Phe(4Cl)²,D-Trp³,D-Lys⁵,D-Ala¹⁰]LHRH (Preparation IV, 33.4 mg), [Ac-D-Nal(2)¹,D-Phe(4Cl)²,D-Trp³,Arg⁵,D-Lys⁶,D-Ala¹⁰] LHRH (Preparation VB, 35.6 mg) and [Ac-D-Nal(2)¹,D-Phe(4Cl)²,D-Pal(3)³,Arg⁵,D-Lys⁶,D-Ala¹⁰]LHRH (Preparation VA, 34.8 mg), the following peptides were prepared:

pGlu-His-Trp-Ser-Tyr-D-Orn(CPC)-Leu-Arg-Pro-Gly-NH$_2$(9) (12.1 mg), [Ac-D-Nal(2)-D-Phe(4Cl)-D-Trp-Ser-Tyr-D-Lys(CPC)-Leu-Arg-Pro-D-Ala-NH$_2$ (16) (24.4 mg), [Ac-D-Nal(2)-D-Phe(4Cl)-D-Trp-Ser-Arg-D-Lys(CPC)-Leu-Arg-Pro-D-Ala-NH$_2$ (20) (10.6 mg), [Ac-D-Nal(2)-D-Phe(4Cl)-D-Pal(3)-Ser-Arg-D-Lys (CPC)-Leu-Arg-Pro-D-Ala-NH$_2$ (27) (8.4 mg).

| Peptide No. | HPLC data Gradient (% B/min) for | | Retention time (Min) |
|---|---|---|---|
| | Purification | Analysis | |
| 02 | 15–35/50 | 20–40/20 | 12.6 |
| 09 | 10–30/40 | 25–45/20 | 9.8 |
| 16 | 40–60/40 | 50–79/20 | 10.3 |
| 20 | 25–50/50 | 45–65/20 | 12.3 |
| 27 | 25–45/40 | 35–55/20 | 13.0 |

EXAMPLE III pGlu-His-Trp-Ser-Tyr-D-Lys(AQMOG)-Leu-Arg-Pro-Gly-NH$_2$ (3)

The synthesis of pGlu-His-Trp-Ser-Tyr-D-Lys (AQMOG)-Leu-Arg-Pro-Gly-NH$_2$ (3) was accomplished by coupling of [D-Lys]⁶LHRH (Preparation IIA, 31.9 mg of the TFA salt) and 2-anthraquinonyl-methylenoxy hemiglutarate (Preparation X) with carbodiimide. A solution (200 μl DMF) with 10.6 mg 2-anthraquinonyl-methylenoxy hemiglutarate and 4.6 mg HOBt was cooled down to 0° C. then reacted with 3.5 μl of DIC. After 15 min, this solution was mixed with the cold solution (200 μl) of 31.9 mg [D-Lys]⁶LHRH (Preparation IIA) (neutralized with TEA) and was kept at 0° C. for 24 hours. When the reaction was not complete, the coupling was repeated with half amount of DIC. The reaction mixture was diluted with water and was subjected to purification as described in Example I to yield 21.6 mg of peptide 3.

Peptides pGlu-His-Trp-Ser-Tyr-D-Orn(AQMOG)-Leu-Arg-Pro-Gly-NH$_2$ (10) (15.4 mg),[Ac-D-Nal(2)-D-Phe(4Cl)-D-Trp-Ser-Tyr-D-Lys(AQMOG)-Leu-Arg-Pro-D-Ala-NH$_2$ (17) (18.2 mg),[Ac-D-Nal(2)-D-Phe(4Cl)-D-Trp-Ser-Arg-D-Lys(AQMOG)-Leu-Arg-Pro-D-Ala-NH$_2$ (21) (20.6 mg), [Ac-D-Nal(2)-D-Phe(4Cl)-D-Pal(3)-Ser-Arg-D-Lys(AQMOG)-Leu-Arg-Pro-D-Ala-NH$_2$ (28) (14.7 mg) were prepared in a similar procedure except that [D-Orn]⁶LHRH (Preparation IIB, 31.6 mg), [Ac-D-Nal(2)¹,D-Phe(4Cl)²,D-Trp³,D-Lys⁶,D-Ala¹⁰]LHRH (Preparation IV, 33.4 mg), [Ac-D-Nal(2)¹,D-Phe(4Cl)²,D-Trp³,Arg⁵,D-Lys⁶,D-Ala¹⁰]LHRH (Preparation VB, 35.6 mg) and [Ac-D-Nal(2)¹,D-Phe(4Cl)²,D-Pal(3)³,Arg⁵,D-Lys⁶,D-Ala¹⁰]LHRH (Preparation VA, 34.8 mg) were used as starting materials.

| Peptide | HPLC data Gradient (% B/min) for | | Retention time |
|---|---|---|---|
| No. | Purification | Analysis | (Min) |
| 03 | 30–50/40 | 45–65/20 | 8.6 |
| 10 | 25–45/40 | 45–65/20 | 8.7 |
| 17 | 50–70/40 | 65–85/20 | 6.3 |
| 21 | 35–65/60 | 65–85/20 | 7.4 |
| 28 | 35–55/40 | 45–65/20 | 7.8 |

EXAMPLE IV pGlu-His-Trp-Ser-Tyr-D-Lys(MTX)-Leu-Arg-Pro-Gly-NH$_2$(4)

Preparation of pGlu-His-Trp-Ser-Tyr-D-Lys(MTX)-Leu-Arg-Pro-Gly-NH$_2$ (4) was performed by acylating of [D-Lys]⁶LHRH with methotrexate (amethopterin). To the solution of 12.0 mg of methotrexate in 100 μl of DMF equivalent of DIC was added at 0° C. After 15 min it was mixed with the neutralized (TEA) solution of 31.9 mg [D-Lys]⁶LHRH (Preparation IIA) and was kept 0° C. overnight. Thereafter the reaction mixture was diluted with water and subjected to HPLC as described in Example II. Two main products with slightly different retention times were isolated (a: 5.2 mg, b: 5.5 mg).

Proceeding in a similar manner but using [D-Orn]⁶LHRH (Preparation IIB, 31.6 mg), [Ac-D-Nal(2)¹,D-Phe(4Cl)²,D-Trp³,D-Lys⁶,D-Ala¹⁰]LHRH (Preparation IV, 33.4 mg), [Ac-D-Nal(2)¹,D-Phe(4Cl)²,D-Trp³,Arg⁵,D-Lys⁶,D-Ala¹⁰]LHRH (Preparation VB, 35.6 mg), [Ac-D-Nal(2)¹,D-Phe(4Cl)²,D-Pal(3)³,Arg⁵,D-Lys⁶,D-Ala¹⁰]LHRH (Preparation VA, 34.8 mg), and [D-Lys(Ahx)]⁶LHRH (Preparation VIII, 35 mg) the following peptides were prepared: pGlu-His-Trp-Ser-Tyr-D-Orn(MTX)-Leu-Arg-Pro-Gly-NH$_2$ (11) (4.3 mg), [Ac-D-Nal(2)-D-Phe(4Cl)-D-Trp-Ser-Tyr-D-Lys(MTX)-Leu-Arg-Pro-D-Ala-NH$_2$ (18) (8.4 mg), [Ac-D-Nal(2)-D-Phe(4Cl)-D-Trp-Ser-Arg-D-Lys (MTX)-Leu-Arg-Pro-D-Ala-NH$_2$ (22) (11.8 mg), [Ac-D-Nal(2)-D-Phe(4Cl)-D-Pal(3)-Ser-Arg-D-Lys(MTX)-Leu-Arg-Pro-D-Ala-NH$_2$ (29) (11.6 mg) and pGlu-His-Trp-Ser-Tyr-D-Orn[Ahx (MTX)]-Leu-Arg-Pro-Gly-NH$_2$ (34) (24 mg).

| Peptide | HPLC data Gradient (% B/min) for | | Retention time |
|---|---|---|---|
| No. | Purification | Analysis | (Min) |
| 04 | 20–40/40 | 20–40/20 | 12.3/12.8 |
| 11 | 15–45/60 | 25–45/20 | 10.1 |
| 18 | 40–60/40 | 45–65/20 | 10.3/10.7 |
| 22 | 25–45/40 | 45–65/20 | 7.1/7.4 |
| 29 | 25–45/40 | 30–50/20 | 11.8 |
| 34 | 20–40/40 | 25–45/20 | 10.9 |

EXAMPLE V

Other Peptides

Peptides pGlu-His-Trp-Ser-Tyr-D-Lys[A$_2$pr(D-Mel)$_2$]-Leu-Arg-Pro-Gly-NH$_2$ (5) (12.4 mg),pGlu-His-Trp-Ser-Tyr-D-Orn[A$_2$pr(D-Mel)$_2$]-Leu-Arg-Pro-Gly-NH$_2$ (12)(11.1 mg),[Ac-D-Nal(2)-D-Phe(4Cl)-D-Trp-Ser-Arg-D-Lys[A$_2$pr (D-Mel)$_2$]-Leu-Arg-Pro-D-Ala-NH$_2$ (23) (5.8 mg), [Ac-D-Nal(2)-D-Phe(4Cl)-D-Pal(3)-Ser-Arg-D-Lys [A$_2$pr(D-Mel)$_2$]-Leu-Arg-Pro-D-Ala-NH$_2$ (30) (10.0 mg) were prepared as described in Example I. with the exception that [D-Lys(A$_2$pr)]⁶LHRH (Preparation IIIA, 35.9 mg), [D-Orn (A$_2$pr)]⁶LHRH (Preparation IIIB, 35.6 mg), [Ac-D-Nal(2)¹,D-Phe(4Cl)²,D-Trp³,Arg⁵,D-Lys(A$_2$pr)⁶,D-Ala¹⁰] LHRH (Preparation VIIB, 39.6 mg) and [Ac-D-Nal (2)¹,D-Phe(4Cl)²,D-Pal(3),Arg⁵,D-Lys(A$_2$pr)⁶,D-Ala¹⁰]LHRH (Preparation VIIA, 38.8 mg) were used as amino components and that the amount of the acylating Boc-D-Mel-OPCP was doubled.

| Peptide | HPLC data Gradient (% B/min) for | | Retention time |
|---|---|---|---|
| No. | Purification | Analysis | (Min) |
| 05 | 30–50/40 | 50–70/20 | 9.8 |
| 12 | 25–45/40 | 50–70/20 | 7.8 |
| 23 | 25–45/40 | 55–70/20 | 9.8 |
| 30 | 40–70/60 | 65–85/20 | 12.3 |
| 28 | 35–55/40 | 45–65/20 | 7.8 |

EXAMPLE VI

Other Peptides

The syntheses of pGlu-His-Trp-Ser-Tyr-D-Lys[A$_2$pr (CPC)$_2$]-Leu-Arg-Pro-Gly-NH$_2$ (6) (8.4 mg), pGlu-His-Trp-Ser-Tyr-D-Orn[A$_2$pr(CPC)$_2$]-Leu-Arg-Pro-Gly-NH$_2$ (13) (9.6 mg), [Ac-D-Nal(2)-D-Phe(4Cl)-D-Trp-Ser-Arg-D-Lys [A$_2$pr(CPC)$_2$]-Leu-Arg-Pro-D-Ala-NH$_2$ (24) (7.6 mg), [Ac-D-Nal(2)-D-Phe(4Cl)-D-Pal(3)-Ser-Arg-D-Lys[A$_2$, pr(CPC)$_2$]-Leu-Arg-Pro-D-Ala-NH$_2$ (31) (6.8 mg) was accomplished as described in example II with the exception that [D-Lys(A$_2$pr)]⁶LHRH (Preparation IIIA, 35.9 mg), [D-Orn(A$_2$pr)]⁶-LHRH (Preparation IIIB, 35.6 mg), [Ac-D-Nal(2)¹,D-Phe(4Cl)²,D-Trp³,Arg⁵,D-Lys(A$_2$pr)⁶,D-Ala¹⁰] LHRH (Preparation VIIB, 39.6 mg) and [Ac-D-Nal(2)¹,D-

Phe(4Cl)$^2$,D-Pal(3)$^3$,Arg$^5$,D-Lys(A$_2$pr)$^6$,D-Ala$^{10}$]LHRH (Preparation VIIA, 38.8 mg) were acylated with two equivalent of cyclopropanecarbonylchloride.

| Peptide No. | HPLC data Gradient (% B/min) for | | Retention time (Min) |
|---|---|---|---|
| | Purification | Analysis | |
| 06 | 15–35/40 | 25–45/20 | 10.6 |
| 13 | 15–35/40 | 25–45/20 | 9.3 |
| 24 | 20–50/60 | 45–65/20 | 11.6 |
| 31 | 20–50/60 | 40–60/20 | 8.7 |

EXAMPLE VII

Other Peptides pGlu-His-Trp-Ser-Tyr-D-Lys[A$_2$pr(AQMOG)$_2$]-Leu-Arg-Pro-Gly-NH$_2$ (7) (4.3 mg), pGlu-His-Trp-Ser-Tyr-D-Orn[A$_2$pr(AQMOG)$_2$]-Leu-Arg-Pro-Gly-NH$_2$(14) (8.9 mg), [Ac-D-Nal(2)-D-Phe(4Cl)-D-Trp-Ser-Arg-D-Lys[A$_2$pr(AQMOG)$_2$]-Leu-Arg-Pro-D-Ala-NH$_2$ (25) (10.7 mg), [Ac-D-Nal(2)-D-Phe(4Cl)-D-Pal(3)-Ser-Arg-D-Lys[A$_2$pr(AQMOG)$_2$]-]Leu-Arg-Pro-D-Ala-NH$_2$ (32) (9.1 mg) were synthesized as described in Example III, except that [D-Lys(A$_2$pr)]$^6$LHRH (Preparation IIIA, 35.9 mg), [D-Orn(A$_2$pr)]$^6$LHRH (Preparation IIIB, 35.6 mg), [Ac-D-Nal(2)$^1$, D-Phe(4Cl)$^2$,D-Trp$^3$, Arg$^5$,D-Lys(A$_2$pr)$^6$,D-Ala$^{10}$]LHRH (Preparation VIIB, 39.6 mg) and [Ac-D-Nal(2)$^1$,D-Phe(4Cl)$^2$,D-Pal(3)$^3$,Arg$^5$,D-Lys(A$_2$pr)$^6$,D-Ala$^{10}$]LHRH (Preparation VIIA, 38.8 mg) were used in a carbodiimide coupling reaction and that two times more 2-anthraquinonyl-methylenoxy hemiglutarate, DIC and HOBt were used.

| Peptide No. | HPLC data Gradient (% B/min) for | | Retention time (Min) |
|---|---|---|---|
| | Purification | Analysis | |
| 07 | 35–65/60 | 50–70/20 | 12.6 |
| 14 | 40–60/40 | 50–70/20 | 10.4 |
| 25 | 40–80/80 | 65–85/20 | 13.9 |
| 32 | 40–70/40 | 60–80/20 | 15.2 |

EXAMPLE VIII pGlu-His-Trp-Ser-D-Lys(Glt-DOX)-Leu-Arg-Pro-Gly-NH$_2$ (33)

The synthesis of pGlu-His-Trp-Ser-D-Lys(Glt-DOX)-Leu-Arg-Pro-Gly-NH$_2$ (33) was performed by coupling the aminosugar moiety of doxorubicin to the glutaryl group of [D-Lys(Glt)]$^6$LHRH. 29.6 mg Preparation IX was dissolved in 200 μl of DMF and reacted with 14 mg doxorubicin and 4 μl of DIC in the presence of 6.2 μl of TEA and 3.3 mg HOBt at 0° C. for overnight. The reaction mixture was subjected to HPLC on Column D with solvent system i (20–50% B in 60 min). HPLC retention time of [D-Lys(Glt-DOX)]$^6$LHRH (20 mg) was 10.5 min using solvent system i in linear gradient mode (30–50% B in 20 min).

EXAMPLE IX

The synthesis of pGlu-His-Trp-Ser-Tyr-D-Lys(NQCE)-Leu-Arg-Pro-Gly-NH$_2$ was accomplished by alkylation of [D-Lys]$^6$LHRH (Preparation IIA) with 5(3-chloro-propionyloxy)-1,4-naphthoquinone. To the solution of [D-Lys]$^6$LHRH (31.9 mg) in 200 μl of DMF, 1.2 equivalent of 5(3-chloro-propionyloxy)-1,4-naphthoquinone is added in the presence of equivalent solid K$_2$CO$_3$. After 24 hours, the reaction mixture was evaporated to a small volume and subjected to HPLC on Column D with solvent system i.

EXAMPLE X

The synthesis of pGlu-His-Trp-Ser-Tyr-D-Lys(Azy)-Leu-Arg-Pro-Gly-NH$_2$ (3) was accomplished by coupling of [D-Lys]$^6$LHRH and Trt-Azy with carbodiimide. The solution (200 μl acetonitrile) of 10.6 mg Trt-Azy and 4.6 mg HOBt was cooled down to 0° C. then reacted with 3.5 μl of DIC. After 15 minutes, this solution was mixed with the cold solution (200 μl) of 31.9 mg [D-Lys]$^6$LHRH (Preparation IIA) (neutralized with TEA) and was kept at 0° C. for 24 hours. The Trt protected peptide was isolated by HPLC on Column D, was detritylated with 80% aqueous acetic acid and repurified on the same column with solvent system ii.

EXAMPLE XI

Preparation of pGlu-His-Trp-Ser-Tyr-D-Lys(EPP)-Leu-Arg-Pro-Gly-NH$_2$ (2) is achieved in an alkylation reaction of [D-Lys]$^6$LHRH (Preparation IIA, 31.9 mg of the TFA salt) with epibromohydrin. To the 200 μl DMF solution of peptide, 4 equivalent of TEA and 3 mg epibromohydrin was added. The reaction mixture was stirred for 24 hours at room temperature and then applied onto Column D for purification.

EXAMPLE XII

Preparation of pGLU-His-Trp-Ser-Tyr-D-Lys(MIT)-Leu-Arg-Pro-Gly-NH$_2$ was performed by acylating mitomycin C with [D-Lys(Glt)]$^6$LHRH. 29.6 mg of Preparation IX was dissolved in 200 μl DMF and reacted with 7 mg mitomycin C and 5 μl of DIC in the presence of 6.2 μl of TEA and 3.3 mg of HOBt to 0° C. for overnight. Thereafter, the reaction mixture was diluted with water and subjected to HPLC on Column D with solvent system ii.

EXAMPLE XIII pGlu-His-Trp-Ser-Tyr-D-Lys(Glt-ESP)-Leu-Arg-Pro-Gly-NH$_2$ was synthesized by coupling [D-Lys]$^6$LHRH with preformed hemiglutaryl-esperamycin (unidentified acylation position(s)). The solution of 2 mg hemiglutaryl-esperamycin (100 μl DMF) and 1.3 mg HOBt was cooled down to 0° C. and reacted with 1 μl of DIC. After 10 minutes, 16 mg of [D-Lys]$^6$LHRH was added in 100 μl neutralized DMF and the reaction mixture was kept at 0° C. for 24 hours. Several products were isolated by HLPC (Column C, solvent system ii).

EXAMPLE XIV

Biological Effects, Receptor Binding Potencies and Cytotoxic Activities.

The biological effects, the receptor binding potencies and the cytotoxic activities of the claimed compounds are summarized in Table 1 to Table 4.

Table 1 shows the hormonal activity of the compounds of this invention having LHRH agonistic properties as compared to that of LHRH in dispersed rat pituitary cell superfusion system in vitro [S. Vigh and A. V. Schally, Peptides 5, 241–247 (1984)]. The peptide was infused for 3 minutes at various concentration, and the amount of LH released was compared to that released by 3 nM LHRH. Table 1 also contains data on the receptor binding affinity of these compounds for human breast cancer cell membranes.

Table 2 presents the antiovulatory activity and human breast cancer cell membrane receptor binding affinity of the claimed compounds having LHRH-inhibiting properties. The inhibitory action was determined in vivo, in 4-day cycling rats as described [A. Corbin and C. W. Beattie, Endocr. Res. Commun., 2, 1–23 (1975)].

Table 3 and 4 shows data on the inhibition of $^3$H-thymidine incorporation into DNA was by cytotoxic LHRH analogs on MCF-7, T47D, MDA-MB-231 and SKBr-3 human mammary cancer cell lines. 200,000 cells in 200 μl of RPMI-160+2% CFBS were incubated with 1, 5 or 10 μg cytotoxic analogs for 3 hours or 23 hours then 1 μCi $^3$H-thymidine added and incubated an additional 60 min. DNA extracted with 1 N perchloric acid and the radioactivity measured.

TABLE 1

LH-releasing activity and receptor binding affinity of pGlu-His-Trp-Ser-Trp-R$^6$(Q)-Leu-Arg-Pro-Gly-NH$_2$ peptides containing cytotoxic radicals for human breast cancer cell membranes.

| | Peptide | | | | Affinity Constant** | |
|---|---|---|---|---|---|---|
| Ex. | R$^6$ | A, (B) | Q$^1$, Q$^2$, Q$^3$, or Q$^4$ | Relative Activity | K$_{a1}$ nM$^{-1}$ | Ka2 uM$^{-1}$ |
| 1. | D-Lys | — | (D-Mel) | | 66.74 | 1.07 |
| 2. | D-Lys | — | CPC | 52 | 1.65 | — |
| 3. | D-Lys | Glt | AQMO | 35 | 1.52 | — |
| 4A. | D-Lys | — | MTX | | 5.42 | 1.59 |
| 4B. | D-Lys | — | MTX | | 0.63 | — |
| 5. | D-Lys | (L-A$_2$pr) | (D-Mel)$_2$ | | 30.48 | 3.45 |
| 6. | D-Lys | (L-A$_2$pr) | (CPC)$_2$ | 25 | 0.14 | — |
| 7. | D-Lys | Glt$_2$, (L-A$_2$pr) | (AQMO)$_2$ | 30 | NB | NB |
| 8. | D-Orn | — | D-Mel | | 11.51 | 0.34 |
| 9. | D-Orn | — | CPC | 40 | — | 44.2 |
| 10. | D-Orn | Glt | AQMO | 56 | — | 1.3 |
| 11. | D-Orn | — | MTX | | | |
| 12. | D-Orn | (L-A$_2$pr) | (D-Mel)$_2$ | | 6.47 | — |
| 13. | D-Orn | (L-A$_2$pr) | (CPC)$_2$ | | NB | NB |
| 14. | D-Orn | Glt$_2$, (L-A$_2$pr) | (AQMO)$_2$ | | | |
| 33. | D-Lys | Glt | DOX | 12 | — | 14.4 |
| 34. | D-Lys | Ahx | MTX | 6.7 | 4.42 | — |

$^{-*}$LH-releasing activity was compared to that produced by 3 nM LH-RH.
**$^{125}$I-[D-Trp]$^6$LHRH used as labelled ligand.

TABLE 2

Antiovulatory activity and affinity of Ac-D-Nal (2)-D-Phe(4Cl)-R$^3$-Ser-R$^5$-D-Lys-(Q)-Leu-Arg-Pro-D-Ala-NH$_2$ peptides containing cytotoxic radicals for membrane receptors of human breast cancer cells.

| | Peptide | | | | % Ovulation Block-ed* | Affinity Constant** | |
|---|---|---|---|---|---|---|---|
| Ex. | R$^3$ | R$^5$ | A, (B) | Q$^1$, Q$^2$, Q$^3$, or Q$^4$ | | K$_{a1}$ nM$^{-1}$ | K$_{a2}$ uM$^{-1}$ |
| 15. | D-Trp | Tyr | — | D-Mel | 100 | 3.58 | — |
| 16. | D-Trp | Tyr | — | CPC | | NB | NB |
| 17. | D-Trp | Tyr | Glt | AQMO | | NB | NB |
| 18. | D-Trp | Tyr | — | MTX | | 3.58 | 1.07 |
| 19. | D-Trp | Arg | — | D-Mel | 40 | — | 32.54 |
| 20. | D-Trp | Arg | — | CPC | 80 | NB | NB |

TABLE 2-continued

Antiovulatory activity and affinity of Ac-D-Nal (2)-D-Phe(4Cl)-R$^3$-Ser-R$^5$-D-Lys-(Q)-Leu-Arg-Pro-D-Ala-NH$_2$ peptides containing cytotoxic radicals for membrane receptors of human breast cancer cells.

| | Peptide | | | | % Ovulation Block-ed* | Affinity Constant** | |
|---|---|---|---|---|---|---|---|
| Ex. | R$^3$ | R$^5$ | A, (B) | Q$^1$, Q$^2$, Q$^3$, or Q$^4$ | | K$_{a1}$ nM$^{-1}$ | K$_{a2}$ uM$^{-1}$ |
| 21. | D-Trp | Arg | Glt | AQMO | 80 | 0.29 | — |
| 22. | D-Trp | Arg | — | MTX | | NB | — |
| 23. | D-Trp | Arg | (L-A$_2$pr) | (D-Mel)$_2$ | | 3.82 | — |
| 24. | D-Trp | Arg | (L-A$_2$pr) | (CPC)$_2$ | 60 | 0.42 | — |
| 25. | D-Trp | Arg | Glt$_2$, (L-A$_2$pr) | (AQMO)$_2$ | 0 | 7.058.6 | — |
| 26. | D-Pal (3) | Arg | — | D-Mel | 100 | 0.97 | 1.34 |
| 27. | D-Pal (3) | Arg | — | CPC | 100 | NB | NB |
| 28. | D-Pal (3) | Arg | Glt | AQMO | 100 | NB | NB |
| 29. | D-Pal (3) | Arg | — | MTX | 100 | 0.44 | 1.04 |
| 30. | D-Pal (3) | Arg | (L-A$_2$pr) | D-Mel)$_2$ | | NB | NB |
| 31. | D-Pal (3) | Arg | (L-A$_2$pr) | (CPC)$_2$ | 100 | 1.52 | — |
| 32. | D-Pal (3) | Arg | Glt$_2$, (L-A$_2$pr) | (AQMO)$_2$ | 40 | 2.28 | — |

*Peptides were tested at 10 μg per rat.
**$^{125}$I-[D-Trp]$^6$ LHRH used as the labelled ligand, NB = no binding

TABLE 3

Inhibitory effect of cytotoxic LHRH analogs of Formula I on $^3$H-Thymidine incorporation into DNA in MCF-7 human breast cancer cell line.

| Ex. | Dose μg/ml | % Inhibition at 4 hrs | % Inhibition at 24 hrs |
|---|---|---|---|
| Control | | 0 | 0 |
| 3 | 1 | 29** | 14** |
| | 10 | 32** | 71** |
| 7 | 1 | 26** | 24** |
| | 10 | 38** | 44** |
| 10 | 1 | 32** | 28** |
| | 5 | 36** | 51** |
| 11 | 1 | 34** | 7 |
| | 10 | 29** | 3 |
| 19 | 1 | | 34** |
| | 10 | | 49** |
| 21 | 1 | | 0 |
| | 10 | | 0 |
| 24 | 1 | 25** | 8 |
| | 10 | 34** | 37** |
| 25 | 1 | | 3 |
| | 10 | | 11 |
| 26 | 1 | 31** | 33** |
| | 10 | 49** | 54** |
| 28 | 1 | | 0 |
| | 10 | | 0 |
| 29 | 1 | | 10 |
| | 10 | | 16 |
| 32 | 1 | 31** | 15 |
| | 10 | 28** | 40** |
| 33 | 1 | 19** | 0 |
| | 5 | 34** | 61** |
| 34 | 1 | | 16 |
| | 10 | | 21 |

**p < 0.01 by Duncan's multiple range test.

TABLE 4

Inhibitory effect of cytotoxic LHRH analogs of Formula I on $^3$H-Thymidine incorporation into DNA in different human breast cancer cell lines.

| Ex. | Dose μg/ml | % Inhibition at 4 hrs | % Inhibition at 24 hrs |
|---|---|---|---|
| T47D Cell line | | | |
| Control | — | 0 | 0 |
| 4 | 1 | 38** | 26 |
|  | 10 | 54** | 41 |
| 5 | 1 | 31** | 15 |
|  | 10 | 39** | 28 |
| 24 | 1 | 44** | 22 |
|  | 10 | 50** | 12 |
| 25 | 1 | 37** | 20 |
|  | 10 | 41** | 54 |
| 33 | 1 | 32** | 11 |
|  | 10 | 44** | 10 |
| MDA-MB-231 Cell Line | | | |
| Control | — | 0 | 0 |
| 4 | 1 | 23* | 0 |
|  | 10 | 31** | 8 |
| 5 | 1 | 20* | 15 |
|  | 10 | 20* | 62** |
| 24 | 1 | 25* | 8 |
|  | 10 | 73** | 11 |
| 25 | 1 | 36** | 0 |
|  | 10 | 40** | 90** |
| 33 | 1 | 20* | 0 |
|  | 10 | 9 | 0 |
| SkBr-3 Cell line | | | |
| Control | — | 0 | 0 |
| 4 | 1 | 21* | 16** |
|  | 10 | 36** | 10 |
| 5 | 1 | 24** | 30** |
|  | 10 | 21** | 66** |
| 24 | 1 | 37** | 18* |
|  | 10 | 42** | 29** |
| 25 | 1 | 30** | 9 |
|  | 10 | 53** | 88** |
| 33 | 1 | 27** | 0 |
|  | 10 | 24** | 14** |

*p < 0.05 by Duncan's multiple range test.
**p < 0.01 by Duncan's multiple range test.

We claim:

1. A peptide selected from the group of peptides having the formula:

$$X-R^1-R^2-R^3-Ser-R^5-R^6(Q)-Leu-Arg-Pro-R^{10}-NH_2$$

wherein $R^1$ is pGlu or D-Nal(2), $R^2$ is His or D-Phe(4Cl), $R^3$ is Trp, D-Trp or D-Pal(3), $R^5$ is Tyr or Arg, $R^6$ is D-Lys or D-Orn, $R^{10}$ is Gly or D-Ala, X is hydrogen or a lower alkanoyl group of 2–5 carbon atoms, Q is a cytotoxic moiety having the formula
—$Q^4$ or —$A(Q^3)$ or —$B(Q^1)_2$ or —$B(AQ^2)_2$
wherein A is —NH—$(CH_2)_n$—CO— or —OC—$(CH_2)_n$—CO—
where n is 2–6, B is —HN—$CH_2$—$(CH_2)_m$—CH(NH)—$(CH_2)_n$—CO— where m is 0 or 1, n is 0 or 1, the —CO moiety of A— and of B— being bonded to the epsilon or delta amino group of $R^6$ when $R^6$ is Lys or Orn respectively, and in the group $B(AQ^2)_2$, the —CO moiety of A being bonded to an amino group on B, $Q^1$ is D or L-melphalanyl, cyclopropanecarbonyl, aziridine-2-carbonyl, epoxyalkyl or 1,4-naphthoquinonyl-5-oxycarbonyl-ethyl, $Q^2$ is $Q^1$, 2-anthraquinonyl-methylenoxy or doxorubicinyl, $Q^3$ is $Q^2$, mitomicinyl, esperamycinyl or methotrexoyl, $Q^4$ is $Q^1$ or methotrexoyl, and pharmaceutically acceptable salts thereof.

2. A peptide of claim 1 wherein Q is $Q^4$.

3. A peptide of claim 2 wherein
$R^1$ is pGlu, $R^2$ is His, $R^3$ is Trp, $R^5$ is Tyr, $R^6$ is D-Lys or D-Orn, $R^{10}$ is Gly and X is hydrogen.

4. A peptide of claim 2 wherein
$R^1$ is D-Nal(2), $R^2$ is D-Phe(4Cl), $R^3$ is D-Trp or D-Pal(3), $R^5$ is Tyr or Arg, $R^6$ is D-Lys or D-Orn, $R^{10}$ is D-Ala and X is a lower alkanoyl group of 2–5 carbon atoms.

5. A peptide of claim 1 wherein Q is $A(Q^3)$.

6. A peptide of claim 5 wherein
$R^1$ is pGlu, $R^2$ is His, $R^3$ is Trp, $R^5$ is Tyr, $R^6$ is D-Lys or D-Orn, $R^{10}$ is Gly and X is hydrogen.

7. A peptide of claim 5 wherein
$R^1$ is D-Nal(2), $R^2$ is D-Phe(4Cl), $R^3$ is D-Trp or D-Pal(3), $R^5$ is Tyr or Arg, $R^6$ is D-Lys or D-Orn, $R^{10}$ is D-Ala and X is a lower alkanoyl group of 2–5 carbon atoms.

8. A peptide of claim 1 wherein Q is $B(Q^1)_2$.

9. A peptide of claim 8 wherein
$R^1$ is pGlu, $R^2$ is His, $R^3$ is Trp, $R^5$ is Tyr, $R^6$ is D-Lys or D-Orn, $R^{10}$ is Gly and X is hydrogen.

10. A peptide of claim 8 wherein
$R^1$ is D-Nal(2), $R^2$ is D-Phe(4Cl), $R^3$ is D-Trp or D-Pal(3), $R^5$ is Tyr or Arg, $R^6$ is D-Lys or D-Orn, $R^{10}$ is D-Ala and X is a lower alkanoyl group of 2–5 carbon atoms.

11. A peptide according to claim 6 wherein Q is 2-anthraquinonyl-methylenoxy-glutaryl.

12. A peptide according to claim 1 wherein X is H or a lower alkanoyl group of 2–5 carbon atoms, A is glutaryl, B is diaminopropionyl, $Q^1$ is D- or L-Mel or CPC: $Q^2$ is $Q^1$, 2-anthraquionyl-methylenoxy, or doxorubicinyl; $Q^3$ is $Q^2$, or methotrexoyl; and $Q^4$ is $Q^1$ or methotrexoyl.

13. A peptide according to claim 2 wherein $Q^4$ is D- or L-Mel, CPC or methotrexoyl.

14. A peptide according to claim 5 wherein A is 6-aminohexanoyl or glutaryl, and $Q^3$ is 2-anthraquinonyl-methylenoxy, doxorubicinyl or methotrexoyl.

15. A peptide of claim 8 wherein $Q^1$ is D-Mel or cyclopropanecarbonyl.

16. A peptide of claim 1 wherein Q is $B(AQ^2)_2$, B is $A_2$pr and A is glutaryl.

17. A peptide of claim 16 wherein
$R^1$ is pGlu, $R^2$ is His, $R^3$ is Trp, $R^5$ is Tyr, $R^6$ is D-Lys or D-Orn, $R^{10}$ is Gly and X is hydrogen.

18. A peptide of claim 16 wherein
$R^1$ is D-Nal(2), $R^2$ is D-Phe(4Cl), $R^3$ is D-Trp or D-Pal(3), $R^5$ is Tyr or Arg, $R^6$ is D-Lys or D-Orn, $R^{10}$ is D-Ala and X is a lower alkanoyl group of 2–5 carbon atoms.

19. A peptide selected from the group consisting of pGlu-His-Trp-Ser-Tyr-D-Lys(AQMOG)-Leu-Arg-Pro-Gly-NH$_2$, pGlu-His-Trp-Ser-Tyr-D-Lys(MTX)-Leu-Arg-Pro-Gly-NH$_2$, Ac-D-Nal(2)-D-Phe(4Cl)-D-Trp-Ser-Arg-D-Lys[A$_2$pr(AQMOG)$_2$]-Leu-Arg-Pro-D-Ala-NH$_2$, and Ac-D-Nal(2)-D-Phe(4Cl)-D-Pal(3)-Ser-Arg-D-Lys[A$_2$pr(AQMOG)$_2$]-Leu-Arg-Pro-D-Ala-NH$_2$.

20. A peptide of claim 19 having the formula pGlu-His-Trp-Ser-Tyr-D-Lys(AQMOG)-Leu-Arg-Pro-Gly-NH$_2$.

21. A peptide of claim 19 having the formula pGlu-His-Trp-Ser-Tyr-D-Lys(MTX)-Leu-Arg-Pro-Gly-NH$_2$.

22. A peptide of claim 19 having the formula

Ac-D-Nal(2)-D-Phe(4Cl)-D-Trp-Ser-Arg-D-Lys[A$_2$pr(AQMOG)$_2$]-Leu-Arg-Pro-D-Ala-NH$_2$.

23. A peptide of claim 19 having the formula

Ac-D-Nal(2)-D-Phe(4Cl)-D-Pal(3)-Ser-Arg-D-Lys[A$_2$pr(AQMOG)$_2$]-Leu-Arg-Pro-D-Ala-NH$_2$.

* * * * *